(12) United States Patent
Chin

(10) Patent No.: US 7,981,133 B2
(45) Date of Patent: *Jul. 19, 2011

(54) TISSUE DISSECTION METHOD

(75) Inventor: Albert K. Chin, Palo Alto, CA (US)

(73) Assignee: MAQUET Cardiovascular, LLC, San Jose, CA (US)

(*) Notice: Subject to any disclaimer, the term of this patent is extended or adjusted under 35 U.S.C. 154(b) by 279 days.

This patent is subject to a terminal disclaimer.

(21) Appl. No.: 11/962,517

(22) Filed: Dec. 21, 2007

(65) Prior Publication Data
US 2009/0024156 A1 Jan. 22, 2009

Related U.S. Application Data

(60) Continuation of application No. 10/267,202, filed on Oct. 8, 2002, now Pat. No. 7,384,423, which is a continuation of application No. 09/750,848, filed on Dec. 27, 2000, now abandoned, which is a continuation of application No. 09/249,249, filed on Feb. 11, 1999, now Pat. No. 6,264,670, which is a division of application No. 08/907,691, filed on Aug. 8, 1997, now Pat. No. 5,980,549, which is a continuation-in-part of application No. 08/593,533, filed on Jan. 24, 1996, now abandoned, which is a continuation of application No. 08/502,494, filed on Jul. 13, 1995, now abandoned.

(51) Int. Cl.
A61B 17/00 (2006.01)
A61B 17/34 (2006.01)

(52) U.S. Cl. .................. 606/190; 606/191; 606/192

(58) Field of Classification Search .......... 606/190, 606/191, 192, 170, 185
See application file for complete search history.

(56) References Cited

U.S. PATENT DOCUMENTS
207,932 A 9/1878 Alvord
1,083,386 A 1/1914 Chapman
(Continued)

FOREIGN PATENT DOCUMENTS
AU 199935034 A1 6/1999
(Continued)

OTHER PUBLICATIONS
U.S. Appl. No. 60/148,130, filed Aug. 10, 1999, Chin.
(Continued)

Primary Examiner — Vy Q Bui
(74) Attorney, Agent, or Firm — Vista IP Law Group, LLP

(57) ABSTRACT

A cannula and surgical methods include a tubular body, for housing an endoscope having a lighted, viewing end disposed near the distal end of the body that is selectively covered by a blunt, transparent, tissue-separating tip. Endoscopic viewing through the tip is enhanced by inner walls that taper to a cusp adjacent the blunt tip in order to reduce visual distortion. Alternatively, a removable or deflectable tip exposes a probe and endoscope to facilitate viewing and dissection of connective tissue and lateral vessels along the course of a blood vessel for subsequent harvesting or other treatment of the isolated blood vessel. The dissection probe includes a partial ring for passing along the vessel and past lateral branching vessels under visualization through the endoscope and the transparent tip. Surgical procedures including making an initial incision, above an artery or other vessel to establish an initial portion of an elongated working cavity of bluntly-dissected tissue. Lateral branches are doubly occluded, and then severed to isolate the vessel for harvesting and use as a graft conduit.

28 Claims, 14 Drawing Sheets

U.S. PATENT DOCUMENTS

| | | |
|---|---|---|
| 1,422,826 A | 7/1922 | Brown |
| 1,683,708 A | 9/1928 | Wappler |
| 1,727,495 A | 9/1929 | Wappler |
| 1,731,069 A | 10/1929 | Herman |
| 1,741,461 A | 12/1929 | Herman |
| 1,798,902 A | 3/1931 | Raney |
| 1,867,624 A | 7/1932 | Hoffman |
| 1,881,250 A | 10/1932 | Tomlinson |
| 1,978,495 A | 10/1934 | Landau |
| 2,001,169 A | 5/1935 | Wallace |
| 2,002,594 A | 5/1935 | Wappler |
| 2,004,559 A | 6/1935 | Wappler et al. |
| 2,011,169 A | 8/1935 | Wappler |
| 2,012,937 A | 9/1935 | Beuoy |
| 2,028,635 A | 1/1936 | Wappler |
| 2,162,681 A | 6/1939 | Ryan |
| 2,220,720 A | 11/1940 | Jett |
| 2,227,727 A | 1/1941 | Leggiadro |
| 2,316,297 A | 4/1943 | Southerland |
| 2,840,070 A | 6/1958 | Tofflemire |
| 2,821,190 A | 1/1959 | Chase |
| 2,868,206 A | 1/1959 | Stoesser |
| 2,944,552 A | 7/1960 | Canon |
| 3,173,418 A | 3/1965 | Baron |
| 3,185,155 A | 5/1965 | Slaten |
| 3,224,320 A | 12/1965 | Knudsen |
| 3,297,022 A | 1/1967 | Wallace |
| 3,313,294 A | 4/1967 | Uddenberg |
| 3,336,916 A | 8/1967 | Edlich |
| 3,357,433 A | 12/1967 | Fourestier et al. |
| 3,437,747 A | 4/1969 | Sheldon |
| 3,556,085 A | 1/1971 | Takahashi |
| 3,568,677 A | 3/1971 | Nolan et al. |
| 3,613,682 A | 10/1971 | Naylor |
| 3,625,202 A | 12/1971 | Oyoshirhara |
| 3,805,793 A | 4/1974 | Wright |
| 3,821,956 A | 7/1974 | Gordhamer |
| 3,835,841 A | 9/1974 | Terada |
| 3,856,016 A | 12/1974 | Davis |
| 3,857,386 A | 12/1974 | Ashbell |
| 3,866,601 A | 2/1975 | Russell |
| 3,882,852 A | 5/1975 | Sinnreich |
| 3,882,854 A | 5/1975 | Hulka |
| 3,934,115 A | 1/1976 | Peterson |
| 3,980,861 A | 9/1976 | Fakunaga |
| RE29,088 E | 12/1976 | Shaw |
| 4,011,872 A | 3/1977 | Komiya |
| 4,031,898 A | 6/1977 | Hiltebrandt et al. |
| 4,038,987 A | 8/1977 | Komiya |
| 4,052,980 A | 10/1977 | Grams et al. |
| 4,132,227 A | 1/1979 | Ibe |
| 4,175,545 A | 11/1979 | Termanini |
| 4,178,920 A | 12/1979 | Cawood et al. |
| 4,190,042 A | 2/1980 | Sinnreich |
| 4,196,734 A | 4/1980 | Harris |
| 4,232,660 A | 11/1980 | Coles |
| 4,254,762 A | 3/1981 | Yoon |
| 4,257,420 A | 3/1981 | Terayama |
| 4,271,839 A | 6/1981 | Fogarty et al. |
| 4,312,353 A | 1/1982 | Shahbabian |
| 4,318,410 A | 3/1982 | Chin |
| 4,319,563 A | 3/1982 | Kubota |
| 4,359,052 A | 11/1982 | Staub |
| 4,362,160 A | 12/1982 | Hiltebrandt |
| 4,369,768 A | 1/1983 | Vukovic |
| 4,372,295 A | 2/1983 | Heckele |
| 4,418,692 A | 12/1983 | Guay |
| 4,423,727 A | 1/1984 | Widran et al. |
| 4,428,746 A | 1/1984 | Mendez |
| 4,440,170 A | 4/1984 | Golden et al. |
| 4,479,497 A | 10/1984 | Fogarty et al. |
| 4,493,321 A | 1/1985 | Leather |
| 4,493,711 A | 1/1985 | Chin et al. |
| 4,499,898 A | 2/1985 | Knepshield |
| 4,499,899 A | 2/1985 | Lyons, III |
| 4,516,574 A | 5/1985 | Hewes, Jr. |
| 4,516,575 A | 5/1985 | Gerhard et al. |
| 4,526,175 A | 7/1985 | Chin et al. |
| 4,556,058 A | 12/1985 | Green |
| 4,557,255 A | 12/1985 | Goodman |
| 4,562,832 A | 1/1986 | Wilder et al. |
| 4,586,919 A | 5/1986 | Taheri |
| 4,587,968 A | 5/1986 | Price |
| 4,597,030 A | 6/1986 | Brody et al. |
| 4,597,389 A | 7/1986 | Ibrahim et al. |
| 4,600,940 A | 7/1986 | Sluyter |
| 4,607,622 A | 8/1986 | Fritch |
| 4,630,609 A | 12/1986 | Chin |
| 4,638,802 A | 1/1987 | Okada |
| 4,646,738 A | 3/1987 | Trott |
| 4,649,917 A | 3/1987 | Karasawa |
| 4,651,733 A | 3/1987 | Mobin-Uddin |
| 4,653,476 A | 3/1987 | Bonnet |
| 4,654,024 A | 3/1987 | Crittenden |
| 4,656,999 A | 4/1987 | Storz |
| 4,657,018 A | 4/1987 | Hakky |
| 4,662,068 A | 5/1987 | Polonsky |
| 4,667,655 A | 5/1987 | Ogiu et al. |
| 4,696,304 A | 9/1987 | Chin |
| 4,700,694 A | 10/1987 | Shishido |
| 4,702,246 A | 10/1987 | Ellis et al. |
| 4,726,370 A | 2/1988 | Karasawa et al. |
| 4,744,363 A | 5/1988 | Hasson |
| 4,745,908 A | 5/1988 | Wardle |
| 4,754,754 A | 7/1988 | Garito et al. |
| 4,759,348 A | 7/1988 | Cawood |
| 4,759,364 A | 7/1988 | Boebel |
| 4,762,120 A | 8/1988 | Hussein |
| 4,768,508 A | 9/1988 | Chin et al. |
| 4,772,093 A | 9/1988 | Abele et al. |
| 4,773,394 A | 9/1988 | Reichstein et al. |
| 4,779,611 A | 10/1988 | Grooters et al. |
| 4,784,133 A | 11/1988 | Mackin |
| 4,793,346 A | 12/1988 | Mindich |
| 4,819,620 A | 4/1989 | Okutsu |
| 4,819,633 A | 4/1989 | Bauer et al. |
| 4,821,718 A | 4/1989 | Uldall |
| 4,838,246 A | 6/1989 | Hahn et al. |
| 4,858,595 A | 8/1989 | Buess et al. |
| 4,862,874 A | 9/1989 | Kellner |
| 4,863,440 A | 9/1989 | Chin et al. |
| 4,865,019 A | 9/1989 | Phillips |
| 4,867,138 A | 9/1989 | Kubota et al. |
| 4,869,268 A | 9/1989 | Yoon |
| 4,874,375 A | 10/1989 | Ellison |
| 4,877,016 A | 10/1989 | Kantor et al. |
| 4,919,129 A | 4/1990 | Weber, Jr. et al. |
| 4,921,483 A | 5/1990 | Wijay et al. |
| 4,924,851 A | 5/1990 | Ognier et al. |
| 4,924,882 A | 5/1990 | Donovan |
| 4,932,952 A | 6/1990 | Wojciechowicz, Jr. |
| 4,936,842 A | 6/1990 | D'Amelio et al. |
| 4,950,278 A | 8/1990 | Sachse et al. |
| 4,959,067 A | 9/1990 | Muller |
| 4,966,583 A | 10/1990 | Debbas |
| 4,966,596 A | 10/1990 | Kuntz et al. |
| 4,985,030 A | 1/1991 | Melzer et al. |
| 4,991,565 A | 2/1991 | Takahashi et al. |
| 4,994,062 A | 2/1991 | Nishigaki et al. |
| 4,997,419 A | 3/1991 | Lakatos et al. |
| 4,997,436 A | 3/1991 | Oberlander |
| 4,998,527 A | 3/1991 | Meyer |
| 4,998,972 A | 3/1991 | Chin et al. |
| 5,002,557 A | 3/1991 | Hasson |
| 5,007,898 A | 4/1991 | Rosenbluth et al. |
| 5,007,907 A | 4/1991 | Nishigaki et al. |
| 5,007,908 A | 4/1991 | Rydell |
| 5,011,490 A | 4/1991 | Fischell et al. |
| 5,013,312 A | 5/1991 | Parins et al. |
| 5,020,514 A | 6/1991 | Heckele |
| 5,025,778 A | 6/1991 | Silverstein et al. |
| 5,026,370 A | 6/1991 | Lottick |
| 5,026,383 A | 6/1991 | Nobles |
| 5,035,232 A | 7/1991 | Lutze et al. |
| 5,037,433 A | 8/1991 | Wilk et al. |
| 5,047,038 A | 9/1991 | Peters et al. |
| 5,049,154 A | 9/1991 | Quadri |

| Patent No. | Date | Inventor |
|---|---|---|
| 5,053,041 A | 10/1991 | Ansari et al. |
| 5,100,420 A | 3/1992 | Green et al. |
| 5,122,152 A | 6/1992 | Mull |
| 5,153,949 A | 10/1992 | Karlsson |
| 5,159,920 A | 11/1992 | Condon et al. |
| 5,163,949 A | 11/1992 | Bonutti |
| 5,171,311 A | 12/1992 | Rydell et al. |
| 5,181,919 A | 1/1993 | Bergman et al. |
| 5,183,463 A | 2/1993 | Debbas |
| 5,183,464 A | 2/1993 | Dubrul et al. |
| 5,188,596 A | 2/1993 | Condon et al. |
| 5,188,630 A | 2/1993 | Christoudias |
| 5,190,541 A | 3/1993 | Abele et al. |
| 5,197,971 A | 3/1993 | Bonutti |
| 5,201,752 A | 4/1993 | Brown et al. |
| 5,213,093 A | 5/1993 | Swindle |
| 5,217,001 A | 6/1993 | Nakao et al. |
| 5,217,441 A | 6/1993 | Shichman |
| 5,230,621 A | 7/1993 | Jacoby |
| 5,242,390 A | 9/1993 | Goldrath |
| 5,251,613 A | 10/1993 | Adair |
| 5,258,006 A | 11/1993 | Rydell et al. |
| 5,259,366 A | 11/1993 | Reydel et al. |
| 5,269,753 A | 12/1993 | Wilk |
| 5,269,785 A | 12/1993 | Bonutti |
| 5,271,380 A | 12/1993 | Riek et al. |
| 5,271,385 A | 12/1993 | Bailey |
| 5,273,026 A | 12/1993 | Wilk |
| 5,275,608 A | 1/1994 | Forman et al. |
| 5,279,546 A | 1/1994 | Mische et al. |
| 5,284,128 A | 2/1994 | Hart |
| 5,284,478 A | 2/1994 | Nobles et al. |
| 5,290,284 A | 3/1994 | Adair |
| 5,300,036 A | 4/1994 | Mueller et al. |
| 5,312,423 A | 5/1994 | Rosenbluth et al. |
| 5,314,440 A | 5/1994 | Shapiro |
| 5,318,564 A | 6/1994 | Eggers |
| 5,318,586 A | 6/1994 | Ereren |
| 5,320,115 A | 6/1994 | Kenna |
| 5,322,503 A | 6/1994 | Desai |
| 5,331,975 A | 7/1994 | Bonutti |
| 5,334,150 A | 8/1994 | Kaali |
| 5,336,231 A | 8/1994 | Adair |
| 5,337,736 A | 8/1994 | Reddy |
| 5,339,803 A | 8/1994 | Mayzels et al. |
| 5,345,927 A | 9/1994 | Bonutti |
| 5,346,503 A | 9/1994 | Chow |
| 5,346,504 A | 9/1994 | Ortiz et al. |
| 5,352,219 A | 10/1994 | Reddy |
| 5,354,291 A | 10/1994 | Bales et al. |
| 5,359,995 A | 11/1994 | Sewell, Jr. |
| 5,366,476 A | 11/1994 | Noda |
| 5,368,015 A | 11/1994 | Wilk |
| 5,368,567 A | 11/1994 | Lee |
| 5,370,109 A | 12/1994 | Cuny |
| 5,373,840 A | 12/1994 | Knighton |
| 5,374,277 A | 12/1994 | Hassler |
| 5,376,076 A | 12/1994 | Kaali |
| 5,380,291 A | 1/1995 | Kaali |
| 5,383,889 A | 1/1995 | Warner et al. |
| 5,385,572 A | 1/1995 | Nobles et al. |
| 5,386,818 A | 2/1995 | Scheebaum et al. |
| 5,391,178 A | 2/1995 | Yapor |
| 5,395,367 A | 3/1995 | Wilk |
| 5,395,383 A | 3/1995 | Adams et al. |
| 5,397,333 A | 3/1995 | Knoepfler |
| 5,397,335 A | 3/1995 | Gresal et al. |
| 5,403,312 A | 4/1995 | Yates et al. |
| 5,411,466 A | 5/1995 | Hess |
| 5,411,483 A | 5/1995 | Loomas et al. |
| 5,417,697 A | 5/1995 | Wilk et al. |
| 5,419,309 A | 5/1995 | Biehl |
| 5,423,813 A | 6/1995 | Kaiser et al. |
| 5,423,842 A | 6/1995 | Michelson |
| 5,424,877 A | 6/1995 | Tsuyuki et al. |
| 5,425,355 A | 6/1995 | Kulick |
| 5,425,357 A | 6/1995 | Moll et al. |
| 5,429,117 A | 7/1995 | McNamara et al. |
| 5,431,151 A | 7/1995 | Riek et al. |
| 5,441,041 A | 8/1995 | Sauer et al. |
| 5,441,498 A | 8/1995 | Perkins |
| 5,447,513 A | 9/1995 | Davison et al. |
| 5,448,990 A | 9/1995 | De Faria-Correa |
| 5,450,842 A | 9/1995 | Tovey et al. |
| 5,452,732 A | 9/1995 | Bircoll |
| 5,460,629 A | 10/1995 | Shlain et al. |
| 5,468,248 A | 11/1995 | Chin et al. |
| 5,474,057 A | 12/1995 | Makower et al. |
| 5,486,155 A | 1/1996 | Muller et al. |
| 5,489,290 A | 2/1996 | Furnish |
| 5,490,836 A | 2/1996 | Desai |
| 5,496,317 A | 3/1996 | Goble et al. |
| 5,496,345 A | 3/1996 | Kieturakis et al. |
| 5,501,654 A | 3/1996 | Failla et al. |
| 5,505,686 A | 4/1996 | Willis et al. |
| 5,507,755 A | 4/1996 | Gresal et al. |
| 5,509,922 A | 4/1996 | Aranyi et al. |
| 5,511,564 A | 4/1996 | Wilk |
| 5,512,037 A | 4/1996 | Russell et al. |
| 5,514,151 A | 5/1996 | Fogarty et al. |
| 5,514,153 A | 5/1996 | Bonutti |
| 5,522,830 A | 6/1996 | Aranyi |
| 5,533,496 A | 7/1996 | De Faria-Correa et al. |
| 5,535,759 A | 7/1996 | Wilk |
| 5,536,251 A | 7/1996 | Evard et al. |
| 5,540,711 A | 7/1996 | Kieturakis et al. |
| 5,549,605 A | 8/1996 | Hahnen |
| 5,549,636 A | 8/1996 | Li |
| 5,549,637 A | 8/1996 | Crainich |
| 5,551,947 A | 9/1996 | Kaali |
| 5,554,101 A | 9/1996 | Matula et al. |
| 5,558,620 A | 9/1996 | Heckele et al. |
| 5,564,615 A | 10/1996 | Bishop et al. |
| 5,569,164 A | 10/1996 | Lurz |
| 5,569,183 A | 10/1996 | Kieturakis |
| 5,569,244 A | 10/1996 | Hahnen |
| 5,569,274 A | 10/1996 | Rapacki et al. |
| 5,569,291 A | 10/1996 | Privitera et al. |
| 5,569,292 A | 10/1996 | Scwemberger et al. |
| 5,571,100 A | 11/1996 | Goble et al. |
| 5,575,756 A | 11/1996 | Karasawa et al. |
| 5,588,581 A | 12/1996 | Conlon et al. |
| 5,591,183 A | 1/1997 | Chin |
| 5,591,192 A | 1/1997 | Pritivera et al. |
| 5,593,418 A | 1/1997 | Mollenauer |
| 5,599,349 A | 2/1997 | D'Amelio |
| 5,601,580 A | 2/1997 | Goldberg et al. |
| 5,601,581 A | 2/1997 | Fogarty et al. |
| 5,601,589 A * | 2/1997 | Fogarty et al. ................ 606/192 |
| 5,607,441 A | 3/1997 | Sierocuk et al. |
| 5,613,947 A | 3/1997 | Chin |
| 5,618,307 A | 4/1997 | Donlon et al. |
| 5,626,587 A | 5/1997 | Bishop et al. |
| 5,630,787 A | 5/1997 | Yabe et al. |
| 5,630,795 A | 5/1997 | Kuramoto et al. |
| 5,630,813 A | 5/1997 | Kieturakis |
| 5,634,584 A | 6/1997 | Okorocha et al. |
| 5,634,924 A | 6/1997 | Turkel et al. |
| 5,653,722 A | 8/1997 | Kieturakis |
| 5,653,726 A | 8/1997 | Kieturakis |
| 5,656,012 A | 8/1997 | Sienkiewicz |
| 5,658,236 A | 8/1997 | Sauer et al. |
| 5,658,282 A | 8/1997 | Daw et al. |
| 5,662,585 A | 9/1997 | Willis et al. |
| 5,662,588 A | 9/1997 | Iida |
| 5,662,662 A | 9/1997 | Bishop et al. |
| 5,665,096 A | 9/1997 | Yoon |
| 5,667,480 A | 9/1997 | Knight et al. |
| 5,667,520 A | 9/1997 | Bonutti |
| 5,669,906 A | 9/1997 | Grossi et al. |
| 5,673,840 A | 10/1997 | Schulze et al. |
| 5,680,982 A | 10/1997 | Schulze et al. |
| 5,683,349 A | 11/1997 | Makower et al. |
| 5,685,820 A | 11/1997 | Riek et al. |
| 5,688,269 A | 11/1997 | Newton et al. |
| 5,690,606 A | 11/1997 | Slotman |
| 5,695,448 A | 12/1997 | Kimura et al. |
| 5,700,236 A | 12/1997 | Sauer et al. |

| Patent No. | Kind | Date | Inventor |
|---|---|---|---|
| 5,702,408 | A | 12/1997 | Wales et al. |
| 5,702,412 | A | 12/1997 | Popov et al. |
| 5,702,417 | A | 12/1997 | Hermann |
| 5,704,372 | A | 1/1998 | Moll |
| 5,704,534 | A | 1/1998 | Huitema et al. |
| 5,707,389 | A | 1/1998 | Louw et al. |
| 5,713,505 | A | 2/1998 | Huitema |
| 5,716,352 | A | 2/1998 | Viola et al. |
| 5,718,714 | A | 2/1998 | Livneh |
| 5,720,761 | A | 2/1998 | Kaali |
| 5,722,934 | A | 3/1998 | Knight et al. |
| 5,725,479 | A | 3/1998 | Knight et al. |
| 5,728,119 | A | 3/1998 | Smith |
| 5,730,748 | A | 3/1998 | Fogarty et al. |
| 5,730,756 | A | 3/1998 | Kieturakis et al. |
| 5,738,628 | A * | 4/1998 | Sierocuk et al. ............ 600/104 |
| 5,743,850 | A | 4/1998 | Moll et al. |
| 5,743,880 | A | 4/1998 | Hlavka |
| 5,749,870 | A | 5/1998 | Gloth et al. |
| 5,752,966 | A | 5/1998 | Chang |
| 5,759,150 | A | 6/1998 | Konou et al. |
| 5,759,183 | A | 6/1998 | VanDusseldorp |
| 5,759,188 | A | 6/1998 | Yoon |
| 5,762,604 | A | 6/1998 | Kieturakis |
| 5,762,606 | A | 6/1998 | Minnich |
| 5,766,169 | A | 6/1998 | Fritzsch et al. |
| 5,766,215 | A | 6/1998 | Muri et al. |
| 5,772,576 | A | 6/1998 | Knighton et al. |
| 5,772,680 | A | 6/1998 | Kieturakis et al. |
| 5,779,728 | A | 7/1998 | Lunsford |
| 5,782,854 | A | 7/1998 | Hermann |
| 5,795,331 | A | 8/1998 | Cragg et al. |
| 5,797,946 | A | 8/1998 | Chin |
| 5,817,013 | A | 10/1998 | Ginn et al. |
| 5,843,121 | A | 12/1998 | Yoon |
| RE36,043 | E | 1/1999 | Knighton |
| 5,857,961 | A | 1/1999 | Vanden Hoek et al. |
| 5,860,997 | A | 1/1999 | Bonutti |
| 5,871,496 | A | 2/1999 | Ginn et al. |
| 5,895,352 | A | 4/1999 | Kleiner |
| 5,895,353 | A | 4/1999 | Lunsford |
| 5,897,487 | A | 4/1999 | Ouchi |
| 5,908,429 | A | 6/1999 | Yoon |
| 5,913,870 | A | 6/1999 | DeFonzo et al. |
| 5,916,213 | A | 6/1999 | Haissaguerre et al. |
| 5,921,993 | A | 7/1999 | Yoon |
| 5,925,058 | A | 7/1999 | Smith |
| 5,928,135 | A | 7/1999 | Knight et al. |
| 5,928,138 | A | 7/1999 | Knight et al. |
| 5,938,620 | A | 8/1999 | Daxer |
| 5,957,923 | A | 9/1999 | Hahnen et al. |
| 5,957,936 | A | 9/1999 | Yoon et al. |
| 5,968,066 | A | 10/1999 | Fogarty et al. |
| 5,980,549 | A | 11/1999 | Chin |
| 5,984,937 | A | 11/1999 | Morse et al. |
| 5,984,938 | A | 11/1999 | Yoon |
| 5,984,939 | A | 11/1999 | Yoon |
| 5,993,384 | A | 11/1999 | Lunsford et al. |
| 6,036,713 | A | 3/2000 | Kieturakis |
| 6,036,714 | A | 3/2000 | Chin |
| 6,059,802 | A | 5/2000 | Ginn |
| 6,071,232 | A | 6/2000 | Knighton |
| 6,080,102 | A | 6/2000 | Konou et al. |
| 6,120,434 | A | 9/2000 | Kimura et al. |
| 6,123,689 | A | 9/2000 | To |
| 6,129,661 | A | 10/2000 | Iafrati et al. |
| 6,162,173 | A | 12/2000 | Chin et al. |
| 6,176,825 | B1 | 1/2001 | Chin et al. |
| 6,186,825 | B1 | 2/2001 | Rogiel et al. |
| 6,234,958 | B1 | 5/2001 | Snoke et al. |
| 6,277,137 | B1 | 8/2001 | Chin |
| 6,312,442 | B1 | 11/2001 | Kieturakis et al. |
| 6,348,037 | B1 | 2/2002 | Chin et al. |
| 6,361,543 | B1 | 3/2002 | Chin et al. |
| 6,387,043 | B1 | 5/2002 | Yoon |
| 6,406,425 | B1 | 6/2002 | Chin et al. |
| 6,478,028 | B1 | 11/2002 | Paolitto et al. |
| 6,488,689 | B1 | 12/2002 | Kaplan et al. |
| 6,520,975 | B2 | 2/2003 | Branco |
| 6,558,313 | B1 | 5/2003 | Knighton et al. |
| 6,562,051 | B1 | 5/2003 | Bolduc |
| 6,648,898 | B1 | 11/2003 | Baxter |
| 6,660,016 | B2 | 12/2003 | Lindsay |
| 6,673,087 | B1 | 1/2004 | Chang |
| 6,702,813 | B1 | 3/2004 | Baxter et al. |
| 6,705,986 | B2 | 3/2004 | Fiegel et al. |
| 6,730,020 | B2 | 5/2004 | Peng et al. |
| 6,749,609 | B1 | 6/2004 | Lunsford |
| 6,752,756 | B2 | 6/2004 | Lunsford et al. |
| 6,762,368 | B2 | 7/2004 | Saputro |
| 6,811,546 | B1 | 11/2004 | Callas |
| 6,814,696 | B1 | 11/2004 | Chang et al. |
| 6,814,743 | B2 | 11/2004 | Chin |
| 6,830,546 | B1 | 12/2004 | Chin et al. |
| 6,884,248 | B2 | 4/2005 | Bolduc |
| 6,899,670 | B2 | 5/2005 | Peng |
| 6,963,792 | B1 | 11/2005 | Green |
| 6,972,028 | B2 | 12/2005 | Chin |
| 6,976,957 | B1 | 12/2005 | Chin et al. |
| 7,033,357 | B2 | 4/2006 | Baxter et al. |
| 7,066,875 | B2 | 6/2006 | Knighton et al. |
| 7,097,665 | B2 | 8/2006 | Stack |
| 7,146,984 | B2 | 12/2006 | Stack |
| 7,211,040 | B2 | 5/2007 | Knighton et al. |
| 7,214,180 | B2 | 5/2007 | Chin |
| 7,226,409 | B2 | 6/2007 | Peng |
| 7,264,587 | B2 | 9/2007 | Chin |
| 7,288,096 | B2 | 10/2007 | Chin |
| 7,326,178 | B1 | 2/2008 | Lunsford et al. |
| 7,344,536 | B1 | 3/2008 | Lunsford |
| 7,364,657 | B2 | 4/2008 | Mandrusov |
| 7,384,423 | B1 | 6/2008 | Chin |
| 7,398,781 | B1 | 7/2008 | Chin |
| 7,431,725 | B2 | 10/2008 | Stack |
| 7,476,198 | B1 | 1/2009 | Chin et al. |
| 7,479,104 | B2 | 1/2009 | Lau |
| 7,485,092 | B1 | 2/2009 | Stewart |
| 2002/0183593 | A1 | 12/2002 | Chin et al. |
| 2003/0187460 | A1 | 10/2003 | Chin |
| 2003/0187461 | A1 | 10/2003 | Chin |
| 2003/0236544 | A1 | 12/2003 | Lunsford |
| 2004/0097792 | A1 | 5/2004 | Moll |
| 2004/0102804 | A1 | 5/2004 | Chin |
| 2004/0153098 | A1 | 8/2004 | Chin |
| 2004/0153101 | A1 | 8/2004 | Bolduc |
| 2004/0181242 | A1 | 9/2004 | Stack |
| 2004/0216748 | A1 | 11/2004 | Chin |
| 2004/0236231 | A1 | 11/2004 | Knighton |
| 2004/0236310 | A1 | 11/2004 | Chin |
| 2005/0192613 | A1 | 9/2005 | Lindsay |
| 2005/0247320 | A1 | 11/2005 | Stack |
| 2005/0261712 | A1 | 11/2005 | Balbierz |
| 2005/0266109 | A1 | 12/2005 | Chin |
| 2005/0267499 | A1 | 12/2005 | Stack |
| 2006/0052660 | A1 | 3/2006 | Chin |
| 2006/0079915 | A1 | 4/2006 | Chin |
| 2006/0116746 | A1 | 6/2006 | Chin |
| 2006/0206121 | A1 | 9/2006 | Chin |
| 2006/0270900 | A1 | 11/2006 | Chin |
| 2006/0271032 | A1 | 11/2006 | Chin |
| 2006/0287574 | A1 | 12/2006 | Chin |
| 2006/0287734 | A1 | 12/2006 | Stack |
| 2007/0060932 | A1 | 3/2007 | Stack |
| 2007/0118206 | A1 | 5/2007 | Colgan |
| 2007/0162067 | A1 | 7/2007 | Lunsford et al. |
| 2007/0198043 | A1 | 8/2007 | Cox |
| 2007/0219571 | A1 | 9/2007 | Balbierz |
| 2007/0238917 | A1 | 10/2007 | Peng |
| 2007/0276432 | A1 | 11/2007 | Stack |
| 2008/0039879 | A1 | 2/2008 | Chin |
| 2008/0065122 | A1 | 3/2008 | Stack |
| 2008/0097523 | A1 | 4/2008 | Bolduc |
| 2008/0103365 | A1 | 5/2008 | Chin et al. |
| 2008/0132892 | A1 | 6/2008 | Lunsford |
| 2008/0145345 | A1 | 6/2008 | Mandrusov |
| 2008/0145469 | A1 | 6/2008 | Chin |

| | | |
|---|---|---|
| 2008/0306333 A1 | 12/2008 | Chin |
| 2008/0306335 A1 | 12/2008 | Lau |
| 2009/0024156 A1 | 1/2009 | Chin |

FOREIGN PATENT DOCUMENTS

| | | |
|---|---|---|
| AU | 1999-42354 | 7/1999 |
| AU | 199942354 A1 | 7/1999 |
| AU | 1999-035034 | 1/2000 |
| AU | 719712 | 8/2000 |
| AU | 2007-203086 | 7/2007 |
| CA | 2 244 164 | 1/1997 |
| CA | 2 274 270 | 12/1999 |
| CA | 2 279 661 | 2/2000 |
| CA | 2 592 766 | 6/2007 |
| DE | 2218901 | 10/1973 |
| DE | 24 15 263 A1 | 10/1975 |
| DE | 2538738 | 3/1976 |
| DE | 2538758 | 3/1977 |
| DE | 2922239 | 12/1980 |
| DE | 3525917 A1 | 2/1986 |
| DE | 3942589 | 7/1991 |
| DE | 3942589 A1 | 7/1991 |
| EP | 0 131 347 | 1/1985 |
| EP | 0 243 714 A2 | 11/1987 |
| EP | 0312767 A1 | 4/1989 |
| EP | 0312787 A1 | 4/1989 |
| EP | 0 341 943 | 11/1989 |
| EP | 0347140 A1 | 12/1989 |
| EP | 0369936 A1 | 5/1990 |
| EP | 0369937 A1 | 5/1990 |
| EP | 0642764 A1 | 3/1995 |
| EP | 0642768 A1 | 3/1995 |
| EP | 0 664 104 | 7/1995 |
| EP | 0 681 811 A2 | 11/1995 |
| EP | 0 409 569 | 1/1997 |
| EP | 0 761 171 | 3/1997 |
| EP | 0 761 171 A2 | 3/1997 |
| EP | 0 761 171 B1 | 3/1997 |
| EP | 00769270 | 4/1997 |
| EP | 0642764 B1 | 12/1997 |
| EP | 0 867 148 | 9/1998 |
| EP | 0 980 673 | 2/2000 |
| EP | 0 980 673 A2 | 2/2000 |
| FR | 1370580 | 12/1964 |
| FR | 2 265 344 | 10/1975 |
| GB | 2 082 459 | 3/1982 |
| GB | 2082459 | 3/1982 |
| GB | 2 195 540 | 4/1988 |
| GB | 2195540 | 4/1988 |
| JP | 7-27043 | 1/1995 |
| JP | 2802244 | 7/1998 |
| JP | 11-172954 | 6/1999 |
| JP | 11-225282 | 8/1999 |
| JP | 2000-037389 | 2/2000 |
| JP | 2007-509702 | 4/2007 |
| JP | 2007-175478 | 7/2007 |
| SU | 112367 | 6/1958 |
| SU | 510235 | 4/1976 |
| SU | 1371689 | 2/1988 |
| SU | 1371689 A1 | 2/1988 |
| WO | WO 91/08710 | 6/1991 |
| WO | WO 92/20291 | 11/1992 |
| WO | WO 94/18881 | 9/1994 |
| WO | WO 95/10982 | 4/1995 |
| WO | WO 95/19737 | 7/1995 |
| WO | WO 96/01130 | 1/1996 |
| WO | WO 96/30072 | 10/1996 |
| WO | WO 96/36287 | 11/1996 |
| WO | WO 97/16125 | 5/1997 |
| WO | WO 97/26831 | 7/1997 |
| WO | WO 97/33522 | 9/1997 |
| WO | WO 97/37701 | 10/1997 |
| WO | WO 98/02084 | 1/1998 |
| WO | WO 98/02102 | 1/1998 |
| WO | WO 98/06451 | 2/1998 |
| WO | WO 00/40139 | 7/2000 |
| WO | WO 00/40160 | 7/2000 |
| WO | WO 03/057062 A2 | 7/2003 |
| WO | WO 03/094758 A1 | 11/2003 |
| WO | WO 03/105706 | 12/2003 |
| WO | WO 2004/066828 A2 | 8/2004 |
| WO | WO 2004/066829 A2 | 8/2004 |
| WO | WO 2004/073506 | 9/2004 |
| WO | WO 2005/006955 A2 | 1/2005 |
| WO | WO 2005/044079 A2 | 5/2005 |

OTHER PUBLICATIONS

U.S. Appl. No. 60/150,737, filed Aug. 25, 1999, Chin.
U.S. Appl. No. 08/269,666, filed Jul. 1, 1994, Chin.
U.S. Appl. No. 08/502,494, filed Mar. 14, 2000, Chin et al.
U.S. Appl. No. 08/593,533, filed Jan. 24, 1996, Chin.
U.S. Appl. No. 09/133,136, filed Aug. 12, 1998, Chin.
U.S. Appl. No. 09/227,393, filed Jan. 8, 1999, Lunsford et al.
U.S. Appl. No. 09/413,012, filed Oct. 5, 1999, Chin et al.
U.S. Appl. No. 09/635,721, filed Aug. 9, 2000, Chin.
U.S. Appl. No. 09/738,608, filed Dec. 14, 2000, Chin.
U.S. Appl. No. 09/739,595, filed Dec. 15, 2000, Chang.
U.S. Appl. No. 09/750,848, filed Dec. 27, 2000, Chin.
U.S. Appl. No. 10/345,666, filed Jan. 16, 2003, Stack.
U.S. Appl. No. 10/371,537, filed Feb. 21, 2003, Beavers.
U.S. Appl. No. 11/962,517, filed Dec. 21, 2007, Chin.
U.S. Appl. No. 90/004,301, filed Jul. 12, 1996, Knighton et al.
Mackenzie, The Use of Laryngoscope in Diseases of the Throat: with an essay on Hoarseness Loss of Voice, and Stridulous Breathing, In Relation to Nervo-Muscular Affection of the Larynx (1869).
Schwyzer, "On Bronchoscopy. With Report of a Case in Which a Foreign Body was Removed from the Right Lower Lobe of a Lung Through a Bronchoscope", Read before the Minnesota Academy of Medicine pp. 194-206 (Dec. 2, 1903).
Mathews, A Treatise on Diseases of the Rectum, Anus, and Signoid Flexure (1903).
Mayo, "The Surgical Treatment of Varicose Veins", The St. Paul Medical Journal, vol. VI, pp. 695-699 (1904).
Fenwick, "A Handbook of Clinical Electric-Light Cystoscopy" (1905).
Carrel et al.., "Uniterminal and Biterminal Venous Transplantations", Surgery, Gynecology and Obstetrics, vol. II, pp. 266-286 (1906).
Mayo, "Treatment of Varicose Veins", Surgery, Gynecology and Obstetrics, pp. 385-388 (1906).
Carrel et al., "Results of the Biterminal Transplantation of Veins", pp. 415-422 (1906).
Jackson, "Endothelioma of the Right Bronchus Removed by Peroral Bronchoscopy", The American Journal of the Medical Sciences, vol. CLIII, pp. 37-375 (1917).
Stern, "Resection of Obstruction at the Vesical Orifice; New Instruments Resectotherm; Resectoscope and New Method", Journal of American Medical Assoiction, vol. 87, No. 21, pp. 1726-1730 (1926).
Chandler, "Internal Pneumolysis: Results of 110 Consecutive Operations", The Lancet, pp. 879-882 (Oct. 19, 1935).
Hurley, "Some Practical Guiding Principles for Closed Pneumonolysis", Canad. M.A.J., vol. 56, pp. 625-627 (Jun. 1947).
Bayliss, "Closed Intrapleural Pneumonolysis", Chest, vol. XIII, pp. 479-515 (1947).
Sarot et al., "Closed Pneumonolysis (Enucleation Technique)", Chest, vol. XVI, No. 5, pp. 509-542 (Nov. 1949).
Morris et al., "Arterial Bypass Below the Knee", Surgery, Gynecology & Obstetrics, vol. 108, pp. 321-332 (Jan.-Jun. 1959).
Hall, "The Great Saphenous Vein Used in Situ as an Arterial Shunt After Extirpation of the Vein Valves", Surgery, vol. 51, No. 4, pp. 492-495 (Apr. 1962).
Linton et al., "Autogenous Saphenous Vein Bypass Grafts in Femoropopliteal Obliterative Arterial Disease", Surgery, vol. 51, No. 1, pp. 62-73 (Jan.-Jun. 1962).
Palva, "Mediastinoscopy—A New Field for Bronchologists", Acta Oto-Laryngologica, vol. 53, Issue 2 & 3 (1961), http://www.informaworld.com/smpp/content.
Lore, "Tender Grip Forceps", The American Journal of Surgery, vol. 104, pp. 84-85 (Jul. 1962).
May et al., "Arterialized in Situ Saphenous Vein", Archives of Surgery, vol. 91, No. 5, pp. 743-750 (Nov. 1965).

Steptoe, "Abdominal Laparoscopy", Laparoscopy in Gynaecology, pp. 13-25 (1967).
Favaloro, "Saphenous Vein Graft in the Surgical Treatment of Coronary Artery Disease", The Journal of Thoracic and Cardiovascular Surgery, vol. 58, No. 2, (Aug. 1969).
Samuels et al., "In Situ Saphenous Vein Arterial Bypass: A Study of the Anatomy Pertinent to its Use in Situ as a Bypass Graft with a Description of a New Venous Valvulatome". The American Surgeon, vol. 34, No. 2, pp. 122-130 (February).
Barner et al., "Late Failure of Arterialized in Situ Saphenous Vein", Archives of Surgery, vol. 99, pp. 781-786 (Dec. 1969).
Effler et al., "The Simple Approach to Direct Coronary Artery Surgery", The Journal of Thoracic and Cardiovascular Surgery, vol. 62, No. 4, pp. 503-510 (Oct. 1971).
Nagovitsyn, "Varicocide Treatment of Varicose Veins of the Lower Extremities" (1971).
Koontz et al., "Factors Influencing Patency of the Autogenous Vein-Femoropoliteal Bypass Grafts: An Analysis of 74 Cases", Surgery, vol. 71, No. 5, pp. 753-759 (May 1972).
Rizk et al., "Vascular Endoscopy", Radiology, vol. 106, No. 1, pp. 33-35 (Jan. 1973).
Balasegaram, "Hepatic Surgery:A Review of a Personal Series of 95 Major Resections", The Australian and New Zealand Journal of Surgery, vol. 42, No. 1, pp. 1-10 (Aug. 1972).
Brody et al., "Changes in Vein Grafts Following Aorto-Coronary Bypass Induced by Pressure and Ischemia", The Journal of Thoracic and Cardiovascular Surgery, vol. 64, No. 6, pp. 847-854 (Dec. 1972).
Jones et al., "Lesions Observed in Arterial Autogenous Vein Grafts", Cardiovascular Surgery, pp. 198-210 (1972).
Kern et al., "The Intimal Proliferation in Aortic-Coronary Saphenous Vein Grafts: Light and electron microscopic studies", American Heart Journal, pp. 771-777 (Dec. 1972).
Crispin et al., "Intravascular Observation and Surgery Using the Flexible Fibrescope", The Lancet, pp. 750-751 (Apr. 7, 1973).
Abbott et al., "Structural Changes During Preparation of Autogenous Venous Grafts", Surgery, vol. 76, No. 6, pp. 1031-1040 (Dec. 1974).
Brook, "A historical review of the histology of patent autogenous vein grafts and vein patches", The Journal of Cardiovascular Surgery, vol. 16, No. 1, pp. 43-52 (Jan.-Feb. 1975).
Shepherd et al., "Physical Characteristics of Venous System in Man", Veins and their Control, pp. 171-172 (1975).
Gittes, "Operative Nephroscopy", J Urol. (Aug. 1976), http://www.ncbi.nlm.nih.gov/sites/entrez.
Cutler et al., "Autologous Saphenous vein femoropopliteal bypass: Analysis of 298 cases", Surgery, vol. 79, No. 3, pp. 325-331 (Mar. 1976).
Lukomsky et al., "Diagnosing Phasic Nature of Pulmonary Carcinoma by Means of Combined Mediastino-Laparoscopy" 1976.
Corson, "Chapter 10: Operating Room Preparation and Basic Techniques", Laparoscopy, pp. 88-102 (1977).
Gottlob, "The preservation of the venous endothelium by <<dissection without touching>> and by an atraumatic technique of vascular anastomosis", Minerva Chirurqica, vol. 32, pp. 693-700 (1977).
Tarlovskaya et al., "Endoscopic Investigations for Determining Lung Cancer Stage" (1978).
Stiles, "Technique of Saphenous vein aorta-coronary bypass grafting", The Journal of Thoracic and Cardiovascular Sugery, vol. 78, No. 2, pp. 305-308 (Aug. 1979).
May et al., "Concluding Remarks on the Therapy of Incompetent Perforating Veins", Perforating Veins, pp. 251-253 (1981).
Szilagyi et al., "Autogenous vein grafting in femoropopliteal atherosclerosis:The limits of its effectiveness", Surgery, vol. 86, No. 6, pp. 836-851 (1979).
Flemma et al., "Complications of Aortocoronary Bypass Grafting", Complications of Intrathoracic Surgery, pp. 167-177 (1979).
Ochsner et al., "The Internal Mammary Artery as a Coronary Artery Bypass Graft", Coronary Heart Surgery, pp. 120-124 (1979).
Buxton et al., "The significance of vein wall thickness and diameter in relation to the patency of femoropopliteal Saphenous vein bypass grafts", Surgery, vol. 87, No. 4, pp. 425-431 (Apr. 1980).
Hofer et al., "Morphologic Studies in Saphenous Vein Grafts for Aorto-coronary Bypass Surgery Part 1: Morphology of the Graft Using Ordinary Surgical Preparation Techniques", The Thoracic and Cardiovascular Surgeon, vol. 29, No. 1, pp. 32-37 (1981).
Bonchek, "Prevention of endothelial damage during preparation of Saphenous veins for bypass grafting", The Journal of Thoracic and Cardiovascular Surgery, vol. 79, No. 6, pp. 911-915 (Jun. 1980).
McGeachie et al.. "Vein to Artery Grafts: A Quantitative Study of Revascularization by Vasa Vasorum and its Relationship to Intimal Hyperplasia", Annals of Surgery, vol. 194, No. 1, pp. 100-107 (Jul. 1981).
Gundry et al., "Intraoperative Trauma to Human Saphenous Veins: Scanning Electron Microscopic Comparison of Preparation Techniques", The Annals of Thoracic Surgery, vol. 30, No. 1, pp. 40-47 (Jul. 1980).
Buchbinder et al., "Comparison of Patency Rate and Structural Change in in Situ and Reversed Vein Arterial Bypass", Journal of Surgical Research, vol. 30, No. 3, pp. 213-222 (Mar. 1981).
Gundry et al., "Optimal preparation techniques for human Saphenous vein grafts", Surgery, vol. 88, No. 6, pp. 785-794 (Dec. 1980).
Moser, "Angioscopic Visualization of Pulmonary Emboli", Chest, vol. 77, No. 2, pp. 198-201 (Feb. 1980).
Ford et al., "Isolation of Adult Canine Venous Endothelium for Tissue Culture", In Vitro, vol. 17, No. 1, pp. 44-50 (Jan. 1980).
Delaria et al., "Leg wound complications associated with coronary revascularization", The Journal of Thoracic and Cardiovascular Surgery, vol. 81, pp. 403-407 (1981).
Fogarty et al.., "Adjunctive Intraoperative Arterial Dilation: Simplified Instrumentation Technique", Archives of Surgery, vol. 116, No. 11, pp. 1391-1398 (Nov. 1981).
Logerfo et al., "An improved technique for preservation endothelial morphology in vein grafts", Surgery, vol. 90, No. 6, pp. 1015-1024 (Dec. 1981).
Greenberg et al., "Vein-Donor-Leg Cellulities After Coronary Artery Bypass Surgery", Annals of Internal Medicine, vol. 97, No. 4, pp. 565-566 (Oct. 1982).
Gunstensen et al., "Intimal Hyperplasia in Autogenous Veins Used for Arterial Replacement", The Canadian Journal of Surgery, vol. 25, No. 2, pp. 158-165 (Mar. 1982).
McGoon, "Incision Decision Advertisement", The Journal of Thoracic and Cardiovascular Surgery, vol. 83, No. 5 (May 1982).
Catinella et al.., "The factors influencing early patency of coronary artery bypass vein grafts: Correlation of angiographic and ultrastructure findings", The Journal of Thoracic Cardiovascular Surgery, vol. 83, No. 5, pp. 686-700 (May 1982).
Feikes et al., "Harvesting and protection of the Saphenous vein associated with early delivery of blood cardioplegia in coronary artery bypass graft surgery", American Heart Journal, vol. 104, No. 2, Part 1, pp. 329-332 (1982).
Leather et al., "The in Situ Saphenous Vein for Arterial Bypass", Biologic and Synthetic Vascular Prostheses, pp. 351-364 (1982).
Sottiurai et al., "Autogenous Vein Grafts: Experimental Studies", Biologic and Synthetic Vascular Prostheses, pp. 311-364 (1982).
Kinney et al., "Transluminal Angioplasty: A Mechanical-Pathophysiological Correlation of its Physical Mechanisms", Radiology, vol. 153, No. 1, pp. 85-89 (Oct. 1984).
Teimourian et al., "Subcutaneous Endoscopy in Suction Lipectomy", Plastic and Reconstructive Surgery, vol. 74, No. 5, pp. 708-711 (Nov. 1984).
Gregory et al., "Composite Grafts: An Alternative to Saphenous Vein for Lower Extremity Arterial Reconstruction", The Journal of Cardiovascular Surgery, vol. 24, No. 1, pp. 53-57 (Jan.-Feb. 1983).
Hufnagel, "Chapter 1: History of Vascular Grafting", Vascular Grafting—Clinical Appliations and Techniques, pp. 1-12 (1983).
Shah et al., "In Situ Saphenous Vein Arterial Bypass", Vascular Grafting: Clinical Applications and Techniques, pp. 133-147 (1983).
Baddour et al., "Recurrent Cellulitis After Coronary Bypass Surgery", The Journal of the American Medical Journal, vol. 251, No. 8, pp. 1049-1052 (Feb. 17, 1984).
Chin et al., "A Physical Measurement of the Mechanisms of Transluminal Angioplasty", Surgery, vol. 95, No. 2, pp. 196-201 (Feb. 1984).
Crew et al., "Carotid Surgery without Angiography", The American Journal of Surgery, vol. 148, pp. 217-220 (Aug. 1984).

Adcock et al., "Optimal Techniques for Harvesting and Preparation of Reversed Autogenous Vein Grafts for Use as Arterial Substitutes: A Review", vol. 96, No. 5. (Nov. 1984).

Rashid et al., "Subcutaneous Technique for Saphenous Vein Harvest", The Annals of Thoracic Surgery, vol. 37, No. 2, p. 169-170 (Feb. 1984).

Ben-Simhon et al., "Vein Harvesting by Long Blunt and Blind Dissection. A Standardized Technique in the Dog", Biomaterials, Medical Devices, and Artificial Organs, vol. 12, No. 1 & 2, pp. 51-66 (1984).

Dorsey, "Haryesting the Greater Saphenous Vein with a Subcutaneous Vein Remover", The Canadian Journal of Surgery, vol. 28, No. 1, pp. 13-14 (Jan. 1985).

Tilanus et al., "Saphenous Vein or PTFE for Femoropopliteal Bypass", Annals of Surgery, vol. 202, No. 6, pp. 780-782 (Dec. 1985).

Dorsey, "Saphenous Vein Harvesting Using a Subcutaneous Vein Remover", Minnesota Medical Association, pp. 195-198 (Mar. 1985).

Baddour, "Delayed Soft Tissue Infections in Saphenous Venectomy Limbs of Coronary Bypass Patients", Infections in Surgery, vol. 4, No. 4, pp. 243-248 (Apr. 1985).

Spears et al., "Coronary Angioscopy During Cardiac Catheterization", Journal of the American College of Cardiology, vol. 6, No. 1, pp. 93-97 (Jul. 1985).

Hulka et al., "Standard Gynecologic Techniques", Textbook of Laparoscopy, (1994).

Hobbs, "A New Approach to Short Saphenous Vein Varicosities", Surgery of Veins, pp. 301-321 (1985).

Nagovitsyn, "Operative Treatment of Acute Thromophlebitis of the Superficial Veins of the Lower Extremities" (1985).

Weaver et al., "The Lesser Saphenous Vein:Autogenous Tissue for Lower Extremity Revascularization", Journal of Vascular Surgery, vol. 5, No. 5, pp. 687-692 (May 1987).

Scher et al., "Prevention and Management of Ischemic Complications of Vein Harvest Incisions in Cardiac Surgery Case Reports", Angiology, The Journal of Vascular Diseases, vol. 37, No. 1, pp. 119-123 (Jan. 1986).

Taylor et al., "Present Status of Reversed Vein Bypass for Lower Extremity", Journal of Vascular Surgery, vol. 3, No. 2, pp. 288-297 (Feb. 1986).

Meldrum-Hanna, "Long Saphenous Vein Harvesting", The Australian and New Zealand Journal of Surgery, vol. 56, No. 12, pp. 923-924 (Dec. 1986).

Raess et al., "Lesser Saphenous Vein as an Alternative Conduit of Choice in Coronary Bypass Operations", The Annals of Thoracic Surgery, vol. 41, No. 3, pp. 334-336 (Mar. 1986).

Sanborn, "Vascular Endoscopy: Current State of the Art", British Medical Bulletin, vol. 42, No. 3, pp. 270-273 (Apr. 1986).

Grundfest et al., "The Current Status of Angioscopy and Laser Angioplasty", Journal of Vascular Surgery, vol. 5, No. 4, pp. 667-673 (Apr. 1987).

Classen et al., "The Impact of Endoscopy", Gastroenterological Endoscopy, pp. 23-26.

Lemaitre et al., "In Situ Grafting Made Easy", Archives of Surgery, vol. 123, No. 1, pp. 101-103 (Jan. 1988).

Fleisher et al., "Angioscopically Monitored Saphenous Vein Valvulotomy", Journal of Vascular Surgery, vol. 4, No. 4, pp. 360-364 (Oct. 1986).

Miller, "Endoscopic Surgery of the Upper Urinary Tract", British Medical Bulletin, vol. 43, No. 3, pp. 274-279 (1986).

Nagovitsyn, "The Endoscopic Correction of the Shin Venous Blood Flow", Vestnik Khriurgii, vol. 137, No. 11, pp. 48-51 (Nov. 1986).

Noera et al., "Microscopic Evaluation in Saphenous Veins Used as Aortocoronary Bypass Grafts", Giornale Italiano di Cardiologia, vol. 16, No. 12, pp. 1037-1042 (Dec. 1986).

Suma et al. "Vein Perfusions System" for Harvesting the Saphenous Vein Graft in Coronary Bypass Surgery, Kyobu Geka. vol. 39, No. 8, pp. 622-623 (Aug. 1986).

Mehigan, "Symposium:Vascular Application of Angioscopy and Lasers", Journal of Vascular Surgery, vol. 5, No. 4, pp. 664-666 (Apr. 1987).

Taylor et al., "Autogenous Reversed Vein Bypass for Lower Extremity Ischemia in Patients with Absent of Inadequate Greater Saphenous Vein", The American Journal of Surgery, vol. 153, pp. 505-510 (May 1987).

Hashizume et al., "Intimal Response of Saphenous Vein to Intraluminal Trauma by Simulated Angioscope Insertion", Journal of Vascular Surgery, vol. 5, No. 6, pp. 862-868 (Jun. 1987).

Spyt, "Harvesting of the Lesser Saphenous Vein", The Annals of Thoracic Surgery, vol. 43, No. 6, p. 691 (Jun. 1987).

White, "Angioscopy and Laser in cardiovascular Surgery: Current Applications and Future Prospects", Aust. N. Z. J. Surg., vol. 58, No. 271-274 (1988).

Matsumoto et al., "Direct Vision Valvulotomy in in Situ Venous Bypass", Surgery Gynecology & Obstetrics, vol. 165, No. 4 (Oct. 1987).

Classen et al., "Electronic Endoscopy—The Latest Technology", Endoscopy, vol. 19, pp. 118-123 (1987).

Delmotte, "The Electronic Video Endoscope of Tomorrow, but First, its Present Status", Acta Endoscopica, vol. 17, No. 2, pp. 89-91 (1987).

Dimitri et al., "A Quick and Atraumatic Method of Autologous Vein Harvesting Using the Subcutaneous Extraluminal Dissector", The Journal of Cardiovascular Sugery, vol. 28, No. 2, pp. 103-111 (Mar.-Apr. 1987).

Secroun, "Future Methods of Endoscopy", Acta Endoscopica, vol. 17, No. 2, pp. 92-95 (1987).

Lannerstad et al., "Effects of Different Graft Preparation Techniques on the Acute Thrombogenicity of Autologous Vein Grafts", European Surgical Research, vol. 19, pp. 395-399 (Nov.-Dec. 1987).

Towne, "Vascular Endoscopy", Perioperative Assessment in Vascular Surgery, pp. 303-313 (1987).

Chin et al., "The Effect of Valvulotomy on the Flow Rate Through the Saphenous Vein Graft: Clinical Implications", Journal of Vascular Surgery, vol. 8, No. 3, pp. 316-320 (Sep. 1988).

Wood, "Locating Previously "Stripped" Venous Systems and Harvesting of Lesser Saphenous Vein", The Annals of Thoracic Surgery, vol. 45, No. 3 (Mar. 1988).

Takemoto, "Electronic Endoscopy: Its Present and Future", Journal of Gastroenterology and Hepatology, vol. 4, pp. 75-80 (1989).

Cardella et al., "Lower-Extremity Venous Thrombosis: Comparison of Venography, Impedance Plethysmography, and Intravenous Manometry", Radiology, vol. 168, No. 1, pp. 109-112 (Jul. 1988).

Citrin et al., "Replacement of the Carotid Artery Using Nonreversed Saphenous Vein", Surgery, Gynecology & Obstetrics, vol. 167, pp. 155-157 (Aug. 1988).

Woelfle et al., "Intraoperative Assessment of in Situ Saphenous Vein Bypass Grafts by Vascular Endoscopy", European Journal Vascular Endovascular Surgery European, vol. 2, pp. 257-262 (Aug. 1988).

Patel et al., "The Use of Fiber-Optic Intraluminal Transillumination for Saphenous Vein Harvesting", Journal of Vascular Surgery, vol. 8, No. 3, pp. 346-348 (Sep. 1988).

Gaudiani et al., "An Improved Technique for the Internal Mammary Artery Coronary Bypass Graft Procedure", Journal of Cardiac Surgery, vol. 3, No. 4, pp. 467-473 (Dec. 1988).

Hauer et al., "Endoscopic Subfascial Dissection of Perforating Veins", Surgical Endoscopy, vol. 2, pp. 5-12 (1988).

Lee et al., "Hazards of Angioscopic Examination: Documentation of Damage to the Arterial Intima", American Heart Journal,vol. 116, No. 6, pp. 1530-1536 (Dec. 1988).

Rey et al., "Electronic Video Endoscopy: Preliminary Results of Imaging Modification", Endoscopy, vol. 20, pp. 8-10 (1988).

Taylor et al., "Reversed vs. In Situ: Is Either the Technique of Choice for Lower Extremity Vein Bypass?", Perspectives in Vascular Surgery, vol. 1. No. 1, pp. 35-59 (1988).

Barnes et al., "Technical Innovations in Nonreversed Translocated Saphenous Vein Bypass", Journal of Vascular Surgery, vol. 9, No. 3, pp. 499-501 (Mar. 1989).

Chin et al., "Technique Using the Fiberoptic Valvulotome for the in Situ Vein Graft", Surgery Gynecology & Obstetrics, vol. 169, No. 3, pp. 255-256 (Sep. 1989).

Hauer, "Diagnosis and surgical management of varicosities", Herz, vol. 14, No. 5, pp. 274-282 (1989).

Fogarty et al., "Combined Thrombectomy and Dilation for the Treatment of Acute Lower Extremity Arterial Thrombosis", Journal of Vascular Surgery, vol. 10 No. 5, pp. 531-534 (Nov. 1989).
Burnand, "Reversed Saphenous Vein for Femoropopliteal Bypass Grafting", Vascular Surgical Techniques an Atlas, pp. 228-234 (1989).
Chin et al., "Angioscopic Preparation for Saphenous Vein in Situ Bypass Grafting", Endovascular Surgery, pp. 74-81 (1989).
Lavee et al., "Complications of Saphenous Vein Harvesting Following Coronary Artery Bypass Surgery", The Journal of Cardiovascular Surgery, vol. 30, No. 6, pp. 989-991 (1989).
Utley et al., "Preoperative Correlates of Impaired Wound Healing After Saphenous Vein Excision", The Journal of Cardiovascular Surgery, vol. 98, No. 1, pp. 147-149 (1989).
Veith et al., Short Vein Grafts in Limb-saving Arterial Reconstructions, Journal of Vascular and Interventional Radiology, vol. 1, No. 1, pp. 57-61 (Nov. 1990).
Louagie et al., "Viability of Long-Term Cryopreserved Human Saphenous Vein", The Journal of Cardiovascular Surgery, vol. 31, No. 1, pp. 92-100 (Jan.-Feb. 1990).
Galloway, Jr. et al., "A new Device for Interactive, Image-Guided Surgery", Medical Imaging V: Image Capture, Formatting, and Display, SPIE—The International Society of Optical Engineering (Feb. 1991).
Myers et. al., "Semi-closed, ex-situ, non-reversed or reversed autogenous vein grafting", The Journal of Cardiovascular Surgery, vol. 32. No. 1, pp. 110-116 (Jan.-Feb. 1991).
Bailey et al., "Laparoscopic Cholecystectomy: Experience with 375 Consecutive Patients", Ann. Surg., vol. 214, No. 4, pp. 531-540 (1991).
The Southern Surgeons Club, "A Prospective Analysis of 1518 Laparoscopic Cholecystectomies", New England Journal of Medicine, vol. 324, pp. 1073-1078 (Apr. 18, 1991).
Clayman et al.., "Laparoscopic Nephrectomy", The New England Journal of Medicine, vol. 324, No. 19, pp. 1370-1371 (May 9, 1991).
Lam, et al., "Surgical Procedures for Uncomplicated ("Routine") Female Stress Incontinence", The Urologic Clinics of North America, vol. 18, No. 2, pp. 327-337 (May 1991).
Couto et al., "Endoscopic ligation of perforator leg veins", The Lancet, vol. 337, p. 1480 (Jun. 15, 1991).
Milgalter et al., "A technique to harvest the inferior epigastric arteries for coronary bypass procedures", Journal of Cardiac Surgery, vol. 6, No. 2, pp. 306-310 (Jun. 1991).
Preising et al., "A Literature Review: Robots in Medicine", _ Engineering in Medicine and Biology (Jun. 1991).
Owen et al., "Endoscopic ligation of perforator leg veins", Lancet, vol. 338, p. 248 (Jul. 27, 1991).
McCollum et al., "A Simple Means of Access for Harvesting the Lesser Saphenous Vein", European Journal Vascular Endovascular Surgery, vol. 5, pp. 469-470 (Aug. 1991).
Feldman, "Laparoscopic Nephrectomy", Journal of Medicine, vol. 325, No. 15, pp. 1110-1111 (Oct. 10, 1991).
Nowzaradan et al., "Laparoscopic Appendectomy for Acute Appendicitis: Indications and Current Use", Journal of Laparoendoscopic Surgery, vol. 1, No. 5, pp. 247-257 (Oct. 1991).
Spaw et al., "Laparoscopic Hernia Repair: The Anatomic Basis", Journal of Laparoendoscopic Surgery, vol. 1, No. 5, pp. 269-277 (Oct. 1991).
Stierli et al., "In Situ Femorodistal Bypass: Novel Technique for Angioscope-Assisted Intraluminal Side-Branch Occlusion and Valvulotomy. A preliminary Report", British Journal of Surgery, vol. 78, No. 11, pp. 1376-1378 (Nov. 1991).
Bailey et al., "Combined Laparoscopic Cholecystectomy and Selective Vagotomy", Surgical Laparoscopy & Endoscopy, vol. 1, No. 1, pp. 45-49 (1991).
Bergamini et al., "Experience with in situ saphenous vein bypass during 1981 to 1989:Determinant factors of long-term patency", p. 37 (1991).
Corbitt, Jr., "Laparoscopic Herniorrhaphy", Surgical Laparoscopy & Endoscopy, vol. 1, No. 1, pp. 23-25 (1991).
Cuschieri, "Variable curvature shape-memory spatula for laparoscopic surgery", Surgical Endoscopy, vol. 5, pp. 179-181 (1991).

Fitzgibbons et al., "Open Laparoscopy", Surgical Laparoscopy, pp. 87-97 (1991).
Fowler et al.., "Laparoscopy-Assisted Sigmoid Resection", Surgical Laparoscopy & Endoscopy, vol. 1, No. 3, pp. 183-188 (1991).
Gazayerli, "The Gazayerli Endoscopic Retractor* Model 1" Surgical Laparoscopy & Endoscopy; vol. 1, No. 2, pp. 98-100 (1991).
Zhila et al., "High Resection of the Left Testicular Vein and Ligation of the Internal Iliac Arteries by Means of Retroperitoneoscope", No. 5 (1991).
Zucker, "Laparoscopic Guided Cholecystectomy With Electrocautery Dissection", Surgical Laparoscopy, pp. 143-182 (1991).
"3rd World Congress of Endoscopic Surgery" (Jun. 18-20, 1992).
Santilli et al., "Comparison of Preoperative Standard Angiography with Preoperative Balloon Occlusion Femoral Angiography of the Lower Extremity", Journal of Investigative Surgery, vol. 6, No. 1, pp. 83-95 (Feb. 1993).
Zucker, Surgical Laparoscopy Update, pp. 59-61 (1993).
Wittens et al., "A New "Closed" in Situ Vein Bypass Technique", European Journal Vascular Endovascular Surgery, vol. 8, pp. 166-170 (1994).
Biglioli et al., "Arterial and Venous Graft Utilization in Reoperative Coronary Artery Surgery", Cardiology and Cardiac Surgery: Current Topics, pp. 399-415 (1993).
Chin et al., "Novel Technique and Instrumentation for Laparoscopic Application of Hemostatic Clips", The Journal of the American Association of Gynecologic Laparoscopists, vol. 1, No. 2, pp. 150-153 (Feb. 1994).
Chin et al., "Gasless Laparoscopy Using a Planar Lifting Technique", Journal of the American College of Surgeons, vol. 178, No. 4, pp. 401-403 (Apr. 1, 1994).
Kavoussi et al., "Telerobotic Assisted Laparoscopic Surgery: Initial Laboratory and Clinical Experience", Urology, vol. 44, No. 1, pp. 15-19 (Jul. 1994).
Van Dijk et al., "A New "Closed" in Situ Vein Bypass Technique Results in a Reduced Wound Complication Rate", European Journal Vascular Endovascular Surgery, vol. 10, pp. 162-167 Aug. 1995).
Lumsden et al., "Subcutaneous, Video-Assisted Saphenous Vein harvest: Report of the first 30 Cases", Cardiovascular Surgery, vol. 4, No. 6, pp. 771-776 (Dec. 1996).
Tighe, Instrumentation for the Operating Room: A Photographic Manual (1994).
Dion et al., "Experimental laparoscopic aortobifemoral bypass", Surgical Endoscopy, vol. 9, pp. 894-897 (1995).
Bowersox et al., "Vascular applications of telepresence surgery: Initial feasibility studies in swine", Journal of Vascular Surgery, vol. 23, No. 2.. pp. 281-287 (Feb. 1996).
Rosenthal, "Endoscopic in Situ Bypass", The Surgical Clinics of North America, vol. 75, No. 4, pp. 703-713 (Aug. 1995).
Nwasokwa et al., "Coronary Artery Bypass Graft Disease", Annals of Internal Medicine, vol. 123, No. 7, pp. 528-545 (Oct. 1995).
Davies et al., "Pathophysiology of Vein Graft Failure: A Review", European Journal Vascular Endovascular Surgery, vol. 9, pp. 7-18 (1995).
Gelijns et al., "From the Scalpel to the Scope: Endoscopic Innovations in Gastroenterology, Gynecology, and Surgery", Sources of Medical Technology: Universities and Industry, vol. V, pp. 67-96 (1995).
Lumsden et al., "Vein Harvest", Endoscopic Plastic Surgery (1995).
Sawaizumi et al., "Endoscopic Microsurgical Anastomosis: Experimental Study of microsurgical anastomosis using an endoscope", Journal of Japan Society of Plastic and Reconstructive Surgery, vol. 15., No. 12, pp. 871-879 (1995).
Tebbetts, Tebbetts Endoplastic Instrument System (1995).
Cusimano, "Minimally Invasive Cardiac Surgery for Removal of the Greater Saphenous Vein", Canadian Journal of Surgery, vol. 39 (Oct. 1996), http://www.cma.ca/index.cfm.ci.
Tevaearai et al., "Minimally Invasive Harvest of the Saphenous Vein for Coronary Artery Bypass Grafting", The Annals of Thoracic Surgery, vol. 63, pp. S119-S121 (1997).
Iafrati et al., "Endoscopic in situ bypass: A gentler dissection", Surgical Endoscopy, vol. 12, pp. 463-465 (1998).

Hannah et al., "Laparoscopic Retropubic Urethropexy", The Journal of the American Association of Gynecologic Laparoscopists, vol. 4, No. 1, pp. 47-52 (Nov. 1996).

EndoCABG System: Innovative instrumentation for endoscopic coronary artery bypass grafting (1996).

Lumsden et al., "Subcutaneous, video-assisted saphenous vein harvest", Perspectives in Vascular Surgery, vol. 7, No. 2, pp. 43-55 (1994).

Allen et al., "Endoscopic Saphenous Vein Harvesting", pp. 265-266 (1997).

McCarthy et al., "Tricuspid Valve Repair with the Cosgrove-Edwards Annuloplasty System", The Annals of Thoracic Surgery, vol. 64, pp. 267-268 (1997).

Jordan et al., "Video-assisted saphenous vein harvest: The evolution of a new technique", Journal of Vascular Surgery, vol. 26, No. 3, pp. 405-414 (Sep. 1997).

Moazami, "Minimally Invasive Greater Saphenous Vein Harvesting for Coronary Artery Bypass Surgery", Surgical Rounds, pp. 94-98 (Mar. 1997).

Johnson et al., "Endoscopic Femoral-Popliteal/Distal Bypas Grafting: A Preliminary Report", Journal of American College of Surgeons, pp. 331-336 (1998).

Pierik et al., "Endoscopic versus open subfacial division of incompetent perforating veins in the treatment of venous leg ulceration: A randomized trial", Journal of Vascular Surgery, vol. 26, No. 6, pp. 1049-1054 (1997).

Davis et al., "Endoscopic Vein Harvest for Coronary Artery Bypass Grafting: Technique and Outcomes", The Journal of Thoracic and Cardiovascular Surgery, vol. 116, No. 2, pp. 228-235(Aug. 1998).

Hallock et al., "An Endoscopic Subcutaneous Dissector for Obtaining Vein Grafts", Annals of Plastic Surgery, vol. 41, No. 6, pp. 595-599 (Dec. 1998).

Morris et al., "Minimally Invasive Saphenous Vein Harvesting", The Annals of Thoracic Surgery, vol. 66, pp. 1026-1028 (1998).

Allen et al., "Endoscopic Versus Traditional Saphenous Vein Harvesting:A Prospective, Randomized Trial", pp. 26-31 (1998).

Stavridis et al., "Minimally Invasive Long Saphenous Vein Harvesting Using a Laryngoscope", The Heart Surgery Forum, vol. 1, pp. 37-40 (Jan. 30, 1998).

Tran et al., "Tunneling versus open harvest technique in obtaining venous conduits for coronary bypass surgery", European Journal of Cardo-thoracic Surgery, vol. 14, pp. 602-606 (1998).

Wilson, "Ethicon Endopath System", Minimally Invasive Vein Harvesting the Second Generation (Jun. 1998).

"Resins Aid in Bypass Surgery", Plastics Engineering, vol. LIV, No. 8 (Aug. 1998).

Dregelid et al., "Endothelial cell injury in human saphenous veins after manipulation and tweezer grasping", Journal of Cardiovascular Surgery, vol. 29, pp. 464-469 (1988).

Voellinger et al., "Video-Assisted Vein Harvest: A Single Institution's Experience of 103 Peripheral Bypass Cases", Vascular Surgery, vol. 32, No. 6, pp. 545-557 (Nov./Dec. 1998).

Akbari et al., "Saphenous Vein Bypass to Pedal Arteries in Diabetic Patients", pp. 227-232 (1998).

Belkin et al., "Nonreversed Saphenous Vein Bypass for Infrainguinal Arterial Reconstruction", Techniques in Vascular and Endovascular Surgery, pp. 233-241 (1998).

Kulbaski et al., "Video-Assisted Saphenous Vein Harvest", Techniques in Vascular and Endovascular Surgery, pp. 91-102 (1998).

Kyo et al., "Endoscopic harvest of saphenous vein graft for coronary artery bypass grafting: Saitama—Olympus technique", European Journal of Cardio-thoracic Surgery, vol. 14, Suppl. 1, pp. S94-S99 (1998).

Lacroix et al., "Classic versus Endoscopic Perforating Vein Surgery:A Retrospective Study", Acia chir bieg, vol. 98, pp. 71-75 (1998).

Stoney et al., "Lower Extremity", Comprehensive Vascular Exposures, pp. 145-182 (1998).

Brown et al., "Heparin Reduced Residual Clot Within the Lumen of Endoscopically Harvested Saphenous Veins", http://www.aats.org/annualmeeting/Abstracts/2007/T7.html (Aug. 6, 2008).

Snowden-Pencer, Inc., "Emory Endoplastic Instruments", Endoscopic Plastic Surgery, pp. 1-10 (1993).

Wengrovitz, "Wound Complications of Autogenous Subcutaneous Infrainguinal Arterial Bypass Surgery: Predisposing Factors and Management", vol. 11, No. 1, pp. 156-163 (Jan. 1990).

Iafrati, "Laparoscopic Cholecystectomy in the Community Hospital, our first 101 cases", Current Surgery, vol. 48, No. 10 (Dec. 1991).

Ashby, "Operative Choledochoscopy in Common Bile Duct Surgery", Annals of the Royal College of Surgeons of England, vol. 67, pp. 279-283 (1985).

Nezhat et al., "Salpingectomy via Laparoscopy: a new surgical approach" Journal of Laparoendoscopic Surgery (1991), http://www.ncbi.nlm.nih.gov/pubmed/1834264.

Gershman et al., "Laparoscopic Pelvic Lymphadenectomy", Journal of Laparoendoscopic Surgery, vol. 1, No. 1 (1990).

Leahy et al., "Minimally Invasive Esophagogastrectomy: An Approach to Esophagogastrectomy Through the Left Thorax", Journal of Laparoendosopic Surgery, vol. 1, No. 1, pp. 59-62 (Nov. 1990).

Towbin et al., "Real-Time US Guidance During Renal Biopsy in Children", Journal of Vascular and Interventional Radiology (1991), http://www.ncbi.nlm.nih.gov/pubmed/1797225.

Cooperman et al.., "Laparoscopic Colon Resection: a case report", J. Laparoendoscopic Surgery 1991, http://www.ncbi.nlm.nih.gov/pubmed/1834273.

Gunther, "Percutaneous Interventions in the Thorax", Journal of Vascular and Interventional Radiology, pp. 379-390 (May 1992).

Zuckerman et al., „Splenopneumopexy: evaluation with splenoportography, Journal of Vascular and Interventional Radiology, vol. 3, No. 1 (Feb. 1992) http://www.ncbi.nlm.nih.gov/pubmed/1540718.

Tyler, "Voluntary Sterilization", American Journal of Public Health, vol. 63, No. 7, pp. 573-575 (Jul. 1973).

Yeager et al., "Surgical Management of Severe Acute Lower Extremity Ischemia", Journal of Vascular Surgery, vol. 15, No. 2, pp. 385-393 (Feb. 1992).

Woelfle et al., "Technique and Results of Vascular Endoscopy in Arterial and Venous Reconstructions", Annals of Vascular Surgery, vol. 6, No. 4, pp. 347-356 (Jul. 1992).

Stierli et al., "Angioscopy-guided semiclosed technique for in situ bypass with a novel flushing valvulotome: Early results", Journal of Vascular Surgery, vol. 15, No. 3, pp. 564-568 (Mar. 1992).

Stahlfeld et al., "Letter to the editor: A simple technique to protect subcutaneous grafts", Journal of Vascular Surgery, p. 1080 (Jun. 1992).

Shah et al., "Is long vein bypass from groin to ankle a durable procedure? An analysis of a ten-year experience", Journal of Vascular Surgery, vol. 15 (1992).

Rosenthal et al., "Endovascular infrainguinal in situ saphenous vein bypass: A multicenter preliminary report", Journal of Vascular Surgery, vol. 16 (1992).

Pietrafitta et al., "An Experimental Technique of Laparoscopic Bowel Resection and Reanastomosis", Surgical Laparoscopy & Endoscopy, vol. 2, No. 3, pp. 205-211 (Sep. 1992).

Pier et al., "Laparoscopic Appendectomy in 625 Cases: From Innovation to Routine", Surgical Laparoscopy & Endoscopy, vol. 1, No. 1 pp. 8-13 (1991).

Pearce et al., "The Use of Angioscopy in the Saphenous Vein Bypass Graft", Technologies in Vascular Surgery, pp. 289-294 (1992).

Narayanan et al., "Experimental Endoscopic Subcutaneous Surgery", Journal of Laparoendoscopic Surgery, vol. 2, No. 3, pp. 179-183 (1992).

McPherson et al., "Intravascular Ultrasound: Principles and Techniques", Technologies in Vascular Surgery, pp. 233-241 (1992).

Jugenheimer et al., "Endoscopic Subfascial Sectioning of Incompetent Perforating Veins in Treatment of Primary Varicosis", World Journal of Surgery, vol. 16, pp. 971-975 (1992).

Harward et al., "The use of arm vein conduits during infrageniculate arterial bypass", Vascular Surgery (1992).

Flinn et al., "A comparative study of angioscopy and completion arteriography after infrainguinal bypass", Tehcnologies iin Vascular Surgery, pp. 295-305 (1992).

Dries et al., "The Influence of Harvesting Technique on Endothelial Preservation in Saphenous Veins", Journal of Surgical Research, vol. 52, No. 3, pp. 219-225 (Mar. 1992).

Taylor et al., "Technique of Reversed Vein Bypass to Distal Leg Arteries", Techniques in Arterial Surgery, pp. 109-122 (1990).
Taylor et al., "Present status of reversed vein bypass grafting: Five-year results of a modern series", Journal of Vascular Surgery, vol. 11, No. 2, pp. 193-206 (Feb. 1990).
Schmidt et al., "A Canine Model of Intimal Hyperplasia (IH) in Autogenous Vein Grafting: A Preliminary Report", Journal of Investigative Surgery, vol. 3, No. 4, pp. 357-364 (1990).
Sadick, "Treatment of Varicose and Telagiectatic Leg Veins with Hypertonic Saline: A Comparative Study of Heparin and Saline", The Journal of Dermatologic Surgery and Oncology, vol. 16, No. 1, pp. 24-28 (Jan. 1990).
Sadick, "Sclerotherapy of Varicose and Telangiectatic Leg Veins: Minimal Sclerosant Concentration of Hypertonic Saline and Its Relationship to Vessel Diameter", The Journal of Dermatologic Surgery and Oncology, vol. 17, pp. 65-70 (1991).
Lamuraglia et al., "Angioscopy guided semiclosed technique for in situ bypass", Journal of Vascular Surgery, vol. 12, No. 5, pp. 601-604 (Nov. 1990).
Knighton et al., "Saphenous Vein in Situ Bypass", The American Journal of Surgery, vol. 160, pp. 294-299 (Sep. 1990).
Feinberg et al., "The use of composite grafts in femorocrural bypasses performed for limb salvage: A review of 108 consecutive case and comparison with 57 in situ saphenous vein bypasses", Journal of Vascular Surgery (1990).
Beretta et al., "Gastroepiploic artery free graft for coronary bypass", European Journal of Cardiothoracic Surgery, vol. 4, pp. 323-328 (1990).
Troidl, "Surgical Endoscopy and Sonography", Surgical Endoscopy, vol. 4, pp. 41-46 (1990).
Cotton, "Biomedical Engineering in Vascular Surgery", Annals of the Royal College of Surgeons of England, vol. 54, pp. 22-32 (1974).
Crispin, "Arterial Endoscopy", Acta Chirurgica Belgica, No. 1, pp. 59-67 (Jan. 1974).
Plecha, "An Improved Method of Harvesting Long Saphenous Vein Grafts", Archives of Surgery, vol. 108, No. 1 (Jan.-Jun. 1974).
Vollmar et al., "Vascular Endoscopy", The Surgical Clinics of North America, vol. 54, No. 1, pp. 111-122 (Feb. 1974).
Fogarty, "Combined thrombectomy and dilation for the treatment of acute lower extremity arterial thrombosis", Journal of Vascular Surgery, vol. 10, No. 4, 530-534 (Oct. 1989).
Blanco, "Resins Aid in Bypass Surgery", Plastics Engineering (Aug. 1998).
O'Neill, "The Effects on Venous Endothelium of Alterations in Blood Flow Through the Vessels in Vein Walls, and the Possible Relation to Thrombosis", Annals of Surgery, vol. 126, No. 3, pp. 270-288 (Sep. 1947).
Matsumoto et al., "Direct Vision Valvulotomy for Nonreversed Vein Graft", Sugery Gynecology & Obstetrics, vol. 165, No. 2, pp. 180-182 (1987).
Hauer, "Surgery of Perforating Veins", Langenbecks Archive Chirurgie Supplement, pp. 464-465 (1992).
Pierik et al., "Subfascial Endoscopic Ligation in the Treatment of Incompetent Perforating Veins", European Journal Vascular Endovascular Surgery, vol. 9, pp. 38-41 (1995).
Gottlob, "Reconstruction of Venous Valves", Venous Valves: Morphology Function Radiology Surgery, pp. 188-213 (1986).
Berci, "Techiques for improving illumination and recording in endoscopy", Optics and Laser Technology, pp. 31-37 (Feb. 1976).
Berci, Endoscopy today and tomorrow (1976).
Shumacker, "Weglowski's Pioneering Vascular Surgery and Barriers to Progress", Current Critical Problems in Vascular Surgery, vol. 3 (1991).
Buchbinder et al., "B-mode Ultrasonic Imaging in the Preoperative Evaluation of Saphenous Vein", The American Journal, vol. 53, No. 7, pp. 368-372 (Jul. 1987).
Hoffmann, "Die subfasziale, endosopische Laser—Perforantes-Dissektion unter Berucksichtigung auch der lateralen Perforansvenen", Vasomed, vol. 9, No. 5 (1997).
Fischer, "Eine neue Generation der Varizenchirurgie", VASA, Band 20, pp. 311-318 (1991).
Jugenheimer et. al., "Ergebnisse der endoskopischen Perforans-Dissektion", Der Chirurg, pp. 625-628 (Aug. 1991).

Kern et al, "Technique of coronary angioscopy" (2008), http://www.uptodate.com/patients/content/topic.do.
Frazee, "Neuroendoscopy Program" (2008), http://neurosurgery.ucla.edu/body.cfm.
"Preceptor", http://dictionary.reference.com/browse/preceptor.
Berci et al., "History of Endoscopy", Surgical Endoscopy, vol. 14, pp. 5-15 (2000).
"Ultrasound and Interventional Techniques", Surgical Endoscopy, vol. 10, No. 1 (Jan. 1996).
"Minimal Invasive Surgery", Surgical Endoscopy: Ultrasound and Interventional Techniques, vol. 10, No. 1 (Jan. 1996).
"The Eyes of the Wolf are Sharper", Surgical Endoscopy: Ultrasound and Interventional Techniques, vol. 10, No. 3 (Mar. 1996).
"Endoscopic suturing made easy", Surgical Endoscopy: Ultrasound and Interventional Techniques, vol. 9, No. 2 (Feb. 1995).
"Instruments for percutaneous nucleotomy and discoscopy", Surgical Endoscopy: Ultrasound and Interventional Techniques, vol. 3, No. 1 (1995).
"Fiberscope for vascular endoscopy", Surgical Endoscopy: Ultrasound and Interventional Techniques, vol. 3, No. 2 (1989).
"Narrow operative approach, atraumatic examination. The Karl Storz Neuro-Endoscope", Surgical Endoscopy vol. 3, No. 3 (1989).
"Fiberscope for vascular endoscopy", Surgical Endoscopy vol. 3, No. 4 (1989).
"New: Universal-Neuro-Endoscope. New application possibilities for Neurosurgery", Surgical Endoscopy vol. 4, No. 1 (1990).
Springer book advertisement, Surgical Endoscopy vol. 4, No. 4 (1990).
Richard Wolf advertisement, Surgical Endoscopy, vol. 5, No. 1 (1991).
"Why do open surgery", Surgical Endoscopy, vol. 5, No. 2 (1991).
"Minimally invasive surgery. Operating proctoscope for anal surgery", Surgical Endoscopy, vol. 5, No. 3 (1991).
"Laparoscopic Surgery . . . the Next Generation", Surgical Endoscopy, Vo. 6, No. 2 (1992).
"There's a Revolution in Surgery. USSC was there in the beginning", Surgical Endoscopy, vol. 6, No. 3 (1992).
"Cuschieri Thoracoscopic Instruments", Surgical Endoscopy, vol. 6, No. 4 (1992).
"Laparoscopic has just turned a new corner . . . ", Surgical Endoscopy, vol. 6, No. 5 (1992).
"Electronic Video Laparoscopy", Surgical Endoscopy, vol. 6, No. 6 (1992).
"Performing a Nissen just got easier, faster, and cheaper", Surgical Endoscopy, vol. 9, No. 9 (1995).
"Easy entry . . . maximizes safety . . . ", Surgical Endoscopy, vol. 9, No. 5 (1995).
"Richard-Allan Medical Has Just Bent the Rules on Endoscopic Cutting", Surgical Endoscopy, vol. 10, No. 9 (1996).
"High quality endoscopic instruments", Surgical Endoscopy, vol. 10, No. 11 (1996).
"Endoscopic Surgery of the Paranasal Sinuses and Anterior Skull Base", Endoscopy, vol. 22, No. 5 (1990).
"Karl Storz—Endoscopes for bronchoscopy", Endoscopy, vol. 23, No. 1 (1991).
"Original Karl-Storz. System Perfection", Endoscopy, vol. 23, No. 3 (1991).
"Minimally invasive surgery.Laparascopic cholecystectomy", Endoscopy, vol. 23, No. 4 (1991).
"Greater Visibility, Lighter Weight", Endoscopy, Vo. 23, No. 5 (1991).
"A Different View on Diagnosis: (Toshiba Medical Systems) and 2 Live International Therapeutic Endoscopy Course in Mexico City Oct. 10-12, 1990", Endoscopy, vol. 22, No. 3 (1990).
ProMIS Line: The complete endoscopy program from AESCULAP, Endoscopy, vol. 28, No. 3 (1996).
"Now you can afford to change your point of view", Endoscopy, vol. 27, No. 3 (1995).
"Karl Storz endoscopes for NEODYM-YAG and C02 lasers", E 1990, Endoscopy, vol. 22, No. 1 (1990).
"Endoscopic Ultrasonography: EUS", Endoscopy, vol. 22, No. 2 (1990).

"A new sense of security in endoscopic ligation", Sugical Laparoscopy & Endoscopy.
"Laparoscopic Surgery . . . the Next Generation." Surgical Laparoscopy & Endoscopy.
"The Olympus Laparoscopic Cholecystectomy System: Resolution for Gallstones with the Leader in Higher Resolution Optics", Surgical Laparoscopy & Endoscopy.
"Cabot Laparoscopic Irrigation System: Dissect/Lase/Cut/Irrigate/Aspirate through a single puncture", Surgical Laparoscopy & Endoscopy.
"Laparoscopic Cholecystectomy: A Minimally Invasive Treatment for Gallbladder Disease", Surgical Laparoscopy & Endoscopy.
"The DaVinci Line", Surgical Laparoscopy & Endoscopy.
Surgical Laparoscopy & Endoscopy, vol. 1 No. 1 (1991).
Surgical Laparoscopy & Endoscopy, vol. 1, No. 2 (1991).
Surgical Laparoscopy & Endoscopy, vol. 1, No. 3 (1991).
Surgical Laparoscopy & Endoscopy, vol. 1, No. 4 (1991).
Surgical Laparoscopy & Endoscopy, vol. 2, No. 1 (1992).
Surgical Laparoscopy & Endoscopy, vol. 2, No. 2 (1992).
Surgical Laparoscopy & Endoscopy, vol. 2, No. 3 (1992).
Surgical Laparoscopy & Endoscopy, vol. 2, No. 4 (1992).
"Karl Storz Take-apart: the fully cleanable cost-effective, modular instrument solution", Surgical Laparoscopy & Endoscopy, vol. 6, No. 1 (1996).
Cuschieri, "How I Do It", Laparoscopic cholecystectomy (Mar. 1999).
"History of Endoscopy" (2008), http://wwww.alexea.org/.
"Laparoscopy" (1998), http://www.ehealthmd.com/library/laparoscopy/LAP_whatis.html.
White et al., Coronary Angioscopy, vol. 22, No. 1, pp. 20-25 (1995).
"If you need a better grasp of endoscopy, Weck;s new Hasson Graspers will let you do more than "pinch an inch"".
Advertisement: Cooper Endoscopy.
"Control at Your Finger Tips: For Advanced Laparoscopic Surgery", Mectra Labs, Inc.
"Nanticoke Advanced Laparoscopic/Thoracoscopic Instruments for the next generation of endoscopic surgery", Cabot Medical.
"Minimally Invasive Surgery: Laparoscopic Cholecystectomy", Karl Storz Endoscopy.
Advertisement: "Our New Line of Weck Instruments Brings the Feel of Open Surgery to Endoscopy", Linvatec Weck Endoscopy.
"Let Olympus Take You Where you Want to Go", Olympus Corporation.
"Beyond Laparoscopic Cholecystectomy: A Hands-On Course".
"The Surgical Expertise Remains in your Hands . . . Now Trust Olympus to be Your Eyes . . . ", Olympus Corporation.
"Special Needs. Special Designs.", Snowden-Pencer.
"The DaVinci Line", DaVinci Medical.
"The Standard for Laparoscopic Surgery", American Surgical Instruments, Inc.
"VirtuoSaph Endoscopic Vein Harvesting System MCVS550", Terumo (product description).
Olympus Endoscopic Accessories Price List, Effective Feb. 15, 1986.
Feldman, "Laparoscopic Nephrectomy", The New England Journal of Medicine, vol. 325, No. 15, pp. 1110-1111 (Oct. 10, 1991).
History of Endoscopy, http://laparoscopy.blogs.com/endoscopyhistory/table_of_contents/.
Kunlin, "Le traitement de l'ischámie arteritique pas la greffe veineuse longue", Revue de Chirurgie, pp. 206-235 (Aug. 1951).
Stanley et al. Autogenous Saphenous Vein as an Arterial Graft:Clinical Status in Stanley JC (ed): Biologic and Synthetic Vascular Prostheses, New York, Gmne and Stratton, Inc. 333-349 (1982).
Cohen et al Indications for Left Ventricular Aneurysmectomy Circulation 1983; 67; 717-722.
Evdokimov et al., "A Combination of Electroacupuncture and Conduction Anesthesia in Operations for Varicose Dilatation of Lower Extremity Veins", ISSN 0042-4625 (1985).
Lofgren Treatment of Long Saphenous Varicosities and Their Recurrence:A Long-Term Follow-Up, Surgery of the Veins, Grune & Stratton (1985).
Meldrum-Hanna et al. An Improved Technique for Long Saphenous Vein Harvesting for Coronary Revascularization, Annals of Thoracic Surgery 1986 42: 90-92.

Gottlob et al. Replacement of Small Veins by Autologous Grafts: Application of an Endothelium-Preserving Technique, *Vasc Endovascular Surg.* 1982: 16: 27 Vienna and New York.
Lukomskii, "Prevention of Post" (1986).
Nagovitsyn, "Endoscopic Coagulation of the Communicating Veins of the Leg in Chronic Venous Insufficiency", Sovetskaia Meditsina, vol. 12, pp. 109-110 (1987).
Buchbinder et al. B-Mode Ultrasonic Imaging in the Preoperative Evaluation of Saphenous Vein, American Surgeon, Jul. 1987, vol. 53, No. 7.
Sottiurari et al. Autogenous Vein Grafts:Experimental Studies, in Stanley JC (ed): Biologic and Synthetic Vascular Prostheses, New York, Gmne and Stratton, Inc. 311-331 (1982).
Hauer, "Operationstechnik der Endoskopischen Subjascialen Discision der Perforansvenen", Chirurg, vol. 58, pp. 172-175 (1987).
Nagovitsyn, "Endoscopic Electrocoagulation of the Communicating Crural Veins", Khirurgiia (Mosk), vol. 12, pp. 60-61 (Dec. 1987).
Devambez et al., "Ecarteur Autostatique Pour Chirurgie de Varices", Phlebologie: Bulletin de la Societe Francaise de Phlegologie (1988).
Nagovitsyn, "Vein-sparing operations combined with endoscopic electrocoagulation of the communicating veins", Vestnik Khirurgii, vol. 140, No. 3, pp. 92-93 (Mar. 1988).
Nagovitsyn, "Prevention of complications for endoscopic correction of the crural venous blood flow", Vestnik Khirurgii, vol. 142, No. 3, pp. 113-115 (Mar. 1989).
Bailey et al., "Laparoscopic Cholecystectomy: Experience with 375 Consecutive Patients", Ann. Surg. (Oct. 1991).
Maignien, "Splénectomie par voie coelioscopique 1 observation", La Presse Médicale (Dec. 21-28, 1991).
Moll, "Historische Anmerkungen zur Entwicklung von Endoskopie and minimal invasiver Operations-technik", Geschichte Medizin (1993).
Markstrom, "Intraoperativ angioskopi via infrainguinal bypass med vena saphena magna in situ", Medicinsk Rapport, vol. 89, No. 49 (1992).
Fischer, "Die chirurgishe Behandlung der Varizen Grundlagen and heutiger Stand: Surgery of Varicose Veins", Scheweiz. Rundshau Med. (PRAXIS), vol. 79, No. 7 (1990).
Devambez et al., "Self-Retaining retractor for surgery of varices", Phlebologie, vol. 41, No. 2, pp. 297-299 (1988).
*Endoscopy* [vol. 22, No. 4, 1990]: Document in German language 1990.
Vandamme, Jean-Pierre and Bonte, Jan, Vascular Anatomy in Abdominal Surgery, Thieme Medical Publishers, Inc. New York (1990).
Swobodnik, Atlas of Ultrasound Anatomy, Thieme Medical Publishers, Inc., New York (1991).
Curriculum Vitae of Albert K. Chin, M.D.
Respondent Terumo Cardiovascular Systems Corporation's Supplemental Responses to Maquet Cardiovascular L.L.C.'s Interrogatory Nos. 29, 32-33, 45-46, 51-62, 64 and 78 [redacted version with attached claim charts] Aug. 15, 2008.
Terumo's Proposed Claim Construction Oct. 31, 2008.
Maquet's Proposed Claim Constructions Oct. 31, 2008.
Maquet's Proposed Claim Constructions with Supporting Authority Nov. 19, 2008.
Order Granting/Denying Request for Reexamination from 90/004,301 Patent Application.
Public Complaint of Maquet Cardiovascular L.L.C. Under Section 337 of the Tariff Act of 1930 as Amended w/all exhibits Apr. 1, 2008.
Public Response of Respondents Terumo Corporation and Terumo Cardiovascular Systems Corporation to the Complaint and Notice of Investigation Jun. 9, 2008.
Public Amended Response of Respondents Terumo Corporation and Terumo Cardiovascular Systems Corporation to the Complaint and Notice of Investigation Oct. 27, 2008.
Respondent Terumo Cardiovascular Systems Corporation's Responses to Maquet Cardiovascular LLC's Seventh Set of Interrogatories (Nos. 91-95) Aug. 15, 2008.
Respondent Terumo Cardiovascular Systems Corporation's I Responses to Maquet Cardiovascular LLC's Third Set of Interrogatories [No. 78] Jun. 30, 2008.

Respondent Terumo Corporation's Responses to Maquet Cardiovascular LLC's Third Set of Interrogatories (No. 78) Jun. 30, 2008.
Respondent Terumo Corporation's Responses to Maquet Cardiovascular LLC's Sixth Set of Interrogatories (Nos. 82-86) Aug. 15, 2008.
File History of U.S. Patent No. Re 36,043.
File History of U.S. Appl. No. 10/897,157.
File History of U.S. Appl. No. 10/052,016.
File History of U.S. Patent No. 7,326,178.
File History of U.S. Patent No. 5,993,384.
File History of U.S. Patent No. 5,895,353.
"Current critical problems in vascular surgery" vol. 3, Ch 11-18, 25, 26, 29-31, 33-36, 45-49, 65, ISBN 0-942219-24-4.
Berci, "Endoscopy", 1976, ISBN 0-8385-2216-5.
"Enter a new realm", 2007, by Boston Scientific Corp.
"Vasoview competitive advantage", 2007, by Boston Scientific Corp.
"VasoView HemoPro endoscopic vessel harvesting system", 2007, by Guidant.
Decision to merge reexamination and reissue proceedings for U.S. Patent No. 5,373,840 (control No. 90/004,301).
Historical Development of VasoView by Albert Chin.
Pending U.S. Appl. No. 10/897,157.
Initial Expert Report of Paul Mitiguy, Oct. 31, 2008.
Customer Needs Assessment.
VasoView Issue.
Memorandum re VasoView Feedback, Aug. 29, 1996.
Memorandum re VasoView Continued Release Plan, Dec. 11, 1996.
Handwritten Notes.
VasoView 2 Thoughts by Scott C. Anderson, Oct. 10, 1996.
Excerpt from Frazier Lab Notebook No. 144, Jun. 9, 1997.
Excerpt from Frazier Lab Notebook No. 152, Jun. 9, 1997.
Clinical Results.
Orbital Dissection Cannula Product Specification, Jun. 7, 1997.
Attachment A PPAQ Approval, Design Review, Design Freeze, Apr. 15, 1997.
VasoView Oribital Dissector Dissection Cannula IFU, Mar. 14, 1997.
Page from Tachi Callas Lab Notebook.
Senior Staff update, May 5, 1997.
Disengagement project Scope for Enhanced Orbital Dissector, Dec. 18, 1997.
Excerpt from Frazier Lab Notebook No. 144, Nov. 3, 1997.
Excerpt from Tachi Callas Lab notebook No. 152, Nov. 3, 1997.
Orbital Dissection Cannula Enhanced Version Product Specification, Nov. 4, 1997.
Attachment A PPAQ Approval, Design Review, Design Freeze, Sep. 15, 1997.
Attachment A, Nov. 4, 1997.
McCoy Lab Notebook No. 166, Sep. 5, 1997.
VasoView III Development Team Market Preference Data Sheet, Sep. 4, 1997.
VasoView Big Balloon & Handle Market Preference Data Sheet, Mar. 11, 1997.
VasoView Balloon Dissection Cannula Product Label.
Product Specification History Dissection Tools, Jun. 27, 1996.
Product Specification for VasoView Dissection Tools (Rev date Apr. 15, 1996).
Memo to file re Monthly Program Review Summaries, Jul. 9, 1996.
Memo to Total Heart Team regarding Notes from Assn of PA Annual meeting, Jan. 26, 1996.
Memo re FMEA Rationale for SVH Balloon Dissection Cannula, Jun. 24, 1996.
VasoView Balloon Dissection System Product Label (OMS-BDS).
Manufacturing Process instruction for Balloon Dissection System.
Chin Memo regarding Saphenous Vein Harvesting.
Memo regarding Design Review Path Freeze Criteria OMS-BDS, Jul. 1, 1996.
Product Specification VasoView Balloon Dissection System, Jun. 21, 1996.
VasoView Balloon Dissection System Design Validation Conclusions, Jul. 10, 1996.
VasoView Balloon Dissection System Market Preference Data Sheet, Jul. 2, 1996.
VasoView Procedure Information.
Outstanding Clinical Questions & MPT Data Sheet.
Email regarding Pig Lab Results, Aug. 4, 1995.
Summary of Clinical, Jul. 3, 1996.
AATS meeting Update.
VasoView Balloon Dissection System Market Preference Data Sheet, May 29, 1996.
Chin Letter to FDA regarding Pre-Market notification 510K for Tapered Tip Balloon Dissection Cannula, Jul. 17, 1995.
VasoView Balloon Dissection System Market Release Meeting, Jul. 11, 1996.
WII Team Meeting, Dec. 4, 1996.
Jeffrey Wayne Baxter deposition transcript, Sep. 26, 2008.
Albert Chin deposition transcript, Sep. 10, 2008.
Edwin Hlavka deposition transcript, Sep. 8, 2008.
John Lunsford deposition transcript, Sep. 24, 2008.
Justin Williams deposition transcript, Oct. 8, 2008.
Eric Willis deposition transcript, Oct. 7, 2008.
Responses of Maquet Cardiovascular, L.L.C. to Respondents Terumo Corporation and Terumo Cardiovascular Systems Corporation's Second Set of Requests for Admission, Nov. 3, 2008.
Supplemental Responses of Maquet Cardiovascular, L.L.C. to Respondents Terumo Corporation and Terumo Cardiovascular Systems Corporation's Requests for Admission Nos. 8-56, Nov. 20, 2008.
Responses of Maquet Cardiovascular, L.L.C. to Respondents Terumo Corporation and Terumo Cardiovascular Systems Corporation's Third Set of Request for Admission, Nov. 24, 2008.
Responses of Maquet Cardiovascular L.L.C. to Certain Interrogatories from Respondents Terumo Corporation and Terumo Cardiovascular Systems Corporation's First Set of Interrogatories [Nos. 3, 5, 7, 12, 23, 45, 48, 49, 59, 62, and 69], May 23, 2008.
Responses of Maquet Cardiovascular L.L.C. to Respondents Terumo Corporation and Terumo Cardiovascular Systems Corporation's First Set of Interrogatories [Nos. 1-78], Jun. 6, 2008.
Supplemental Responses of Maquet Cardiovasular L.L.C. to Respondents Terumo Corporation and Terumo Cardiovascular Systems Corporation's Interrogatory Nos. [5, 6, 8, 14, 32, 33 & 67], Jul. 23, 2008.
Supplemental Responses of Maquet Cardiovascular L.L.C. to Respondents Terumo Corporation and Terumo Cardiovascular Systems Corporation's Interrogatory No. 21, Sep. 5, 2008.
Responses of Maquet Cardiovascular L.L.C. to Respondents Terumo Corporation and Terumo Cardiovascular Systems Corporation's Third Set of Interrogatories [Nos. 87-115], Aug. 6, 2008.
Responses of Maquet Cardiovascular L.L.C. to Respondents Terumo Corporation and Terumo Cardiovascular Systems Corporation's Fourth Set of Interrogatories [Nos. 116-148], Aug. 11, 2008.
Supplemental Responses of Maquet Cardiovascular L.L.C. to Respondents Terumo Corporation and Terumo Cardiovascular Systems Corporation's Fourth Set of Interrogatories, Sep. 12, 2008.
Second Supplemental Responses of Maquet Cardiovascular L.L.C. to Respondents Terumo Corporation and Terumo Cardiovascular Systems Corporation's Interrogatory Nos. 130, 131, 133, 134, 136 & 137, Oct. 21, 2008.
Supplemental Response of Maquet Cardiovascular L.L.C. to Respondents Terumo Corporation and Terumo Cardiovascular Systems Corporation's Interrogatory Nos. 146 & 148, Oct. 31, 2008.
Responses of Maquet Cardiovascular L.L.C. to Respondents Terumo Corporation and Terumo Cardiovascular Systems Corporation's Fifth Set of Interrogatories [Nos. 149-152], Sep. 5, 2008.
Responses of Maquet Cardiovascular L.L.C. to Respondents Terumo Corporation and Terumo Cardiovascular Systems Corporation's Sixth Set of Interrogatories [Nos. 153-155], Sep. 10, 2008.
Responses of Maquet Cardiovascular L.L.C. to Respondents Terumo Corporation and Terumo Cardiovascular Systems Corporation's Seventh Set of Interrogatories, Nov. 21, 2008.
Responses of Maquet Cardiovascular L.L.C. to Respondents Terumo Corporation and Terumo Cardiovascular Systems Corporation's Eighth Set of Interrogatories, Nov. 24, 2008.
DeLaria, G.A., et al., "Leg Wound Complications Associated With Coronary Revascularization," J. Thorac. Cardiovasc. Surg., 81:403-407, 1981.

Dimitri, W.R., et al., "A Quick and Atraumatic Method of Autologous Vein Harvesting Using the Subcutaneous Extraluminal Dissector," J. Cardiovasc. Surg., 28:103-11, 1987.

Gardiner, B.N., et al., Extraperitoneal Laparoscopic Hernia Repair: Experience in 178 Patients, Surgical Technology International III, International Developments in Surgery and Surgical Research, 1994, pp. 237-242.

Fogarty, M.D., et al., "Selected Applications of Balloon Dissection"; Surgical Technology International III, International Developments in Surgery and Surgical Research, 1994, pp. 45-52.

Hauer, G., et al., "Endoscopic Subfascial Discission of Perforating Veins," Surg. Endosc., 2:5-12, 1988.

Incision Decision, Atrium Medical Corporation advertisement, appearing in J. Thorac. Cardiovasc. Surg., 83(4), 1982.

Meldrum-Hanna, W., et al., "Long Saphenous Vein Harvesting," J. Surg., 56:923-924, 1986.

Moazami, N., M.D., et al., "Minimally Invasive Greater Saphenous Vein Harvesting for Coronary Artery Bypass Surgery," Surgical Rounds, pp. 94-98, Mar. 1997.

Rashid, A., et al., "Subcutaneous Technique for Saphenous Vein Harvest," Ann. Thorac. Surg., 37(2):169-170, 1984.

Saphenous Vein Grafts Are No. 1. Period, Atrium Medical Corporation advertisement, appearing in J. Thorac. Cardiovasc. Surg., 82(6), 1981.

Wheatley, D.J., M.D., ed., "Surgery of Coronary Artery Disease," C.V. Mosby Company, pp. 348-349, pp. 374-375.

* cited by examiner

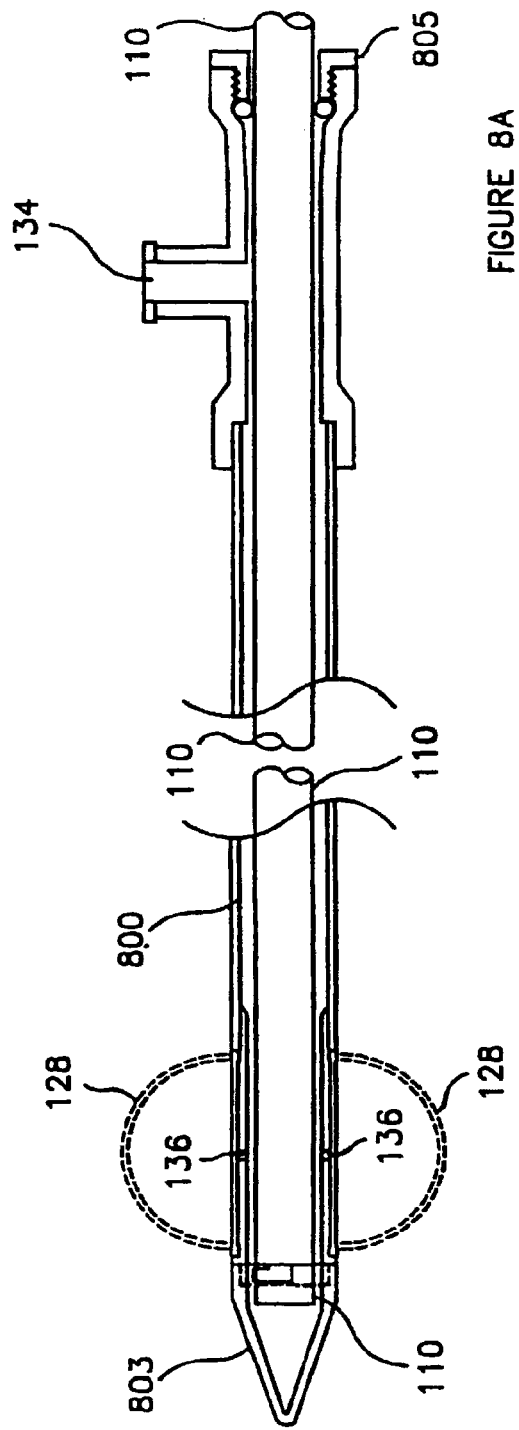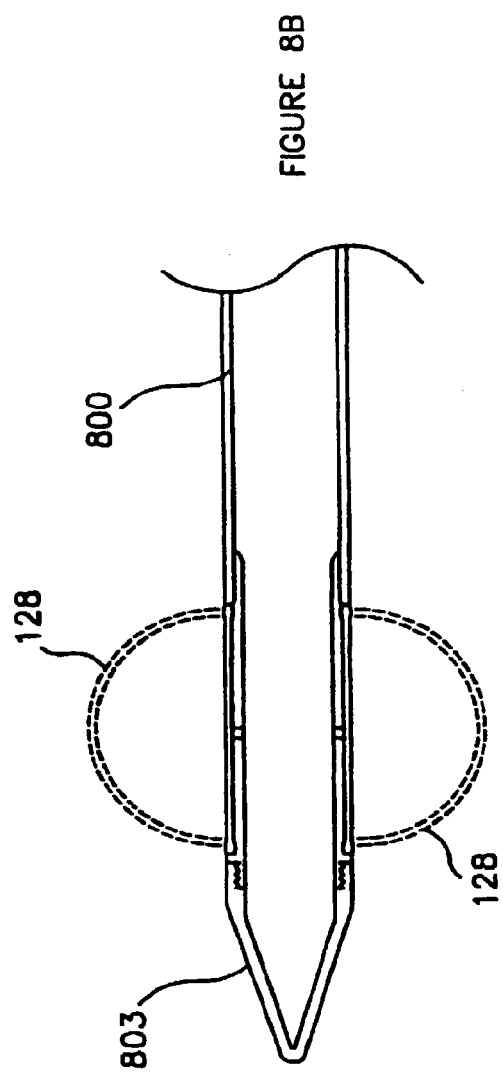
FIGURE 8A
FIGURE 8B

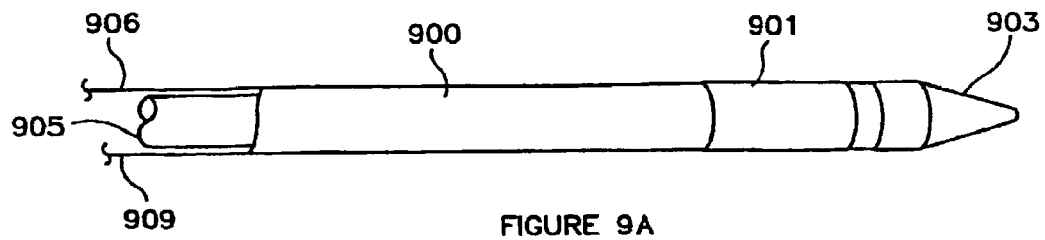
FIGURE 9A
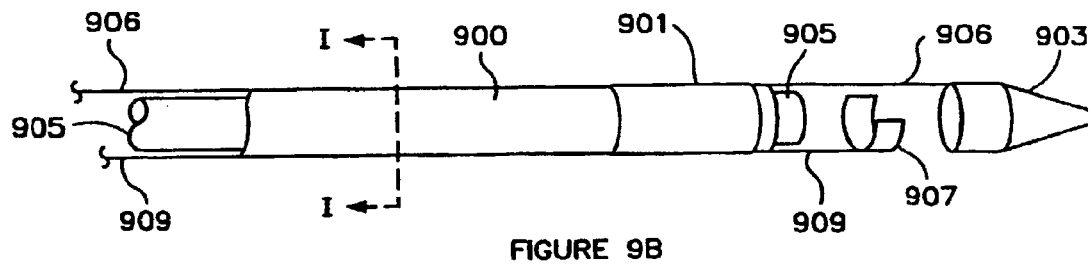
FIGURE 9B
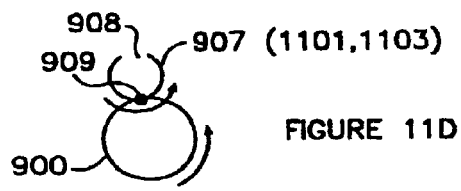
FIGURE 11D
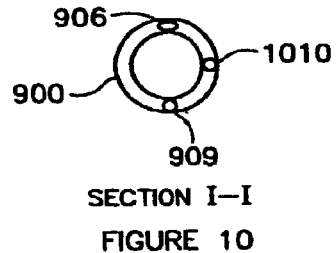
SECTION I—I
FIGURE 10
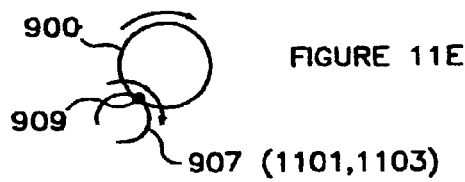
FIGURE 11E
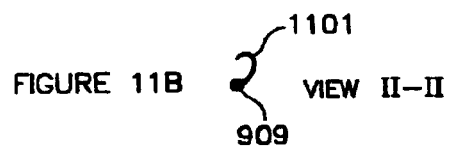
FIGURE 11B    VIEW II—II
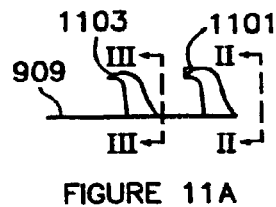
FIGURE 11A
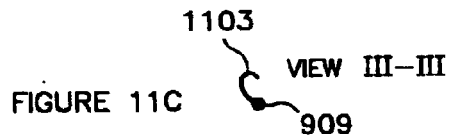
FIGURE 11C    VIEW III—III

TISSUE DISSECTION METHOD

RELATED APPLICATION

This application is a continuation of application Ser. No. 10/267,202, filed on Oct. 8, 2002 which is a continuation of application Ser. No. 09/750,848, filed on Dec. 27, 2000, now abandoned, which is a continuation of Ser. No. 09/249,249, filed on Feb. 11, 1999, and now issued as U.S. Pat. No. 6,264,670, which is a divisional application of application Ser. No. 08/907,691 filed on Aug. 8, 1997, and now issued as U.S. Pat. No. 5,980,549, which is a continuation-in-part application of application Ser. No. 08/593,533 filed on Jan. 24, 1996, now also abandoned, which is a continuation of application Ser. No. 08/502,494, filed on Jul. 13, 1995, now issued as U.S. Pat. No. 5,683,409, and the subject matter hereof is related to the subject matter of application Ser. No. 08/421,481, filed on Apr. 12, 1995, now issued as U.S. Pat. No. 5,591,183, which prior applications are assigned to the same assignee as the present application.

FIELD OF THE INVENTION

The present invention relates generally to a tissue separation cannula used for forming an elongated cavity in tissue planes particularly along the course of a small blood vessel, and more specifically relates to a cannula having an endoscope for continuously visualizing the blunt dissection site through a tissue separating member which is transparent and has a tapered shape and is selectively removable from the cannula to facilitate dissection of tissue adjacent a blood vessel.

DESCRIPTION OF THE BACKGROUND ART

Present methods for the formation of an elongated cavity involve the use of blunt probes that are pushed through body tissue to accomplish the tissue dissection. The force exerted by the passage of mechanical probes may lead to blood vessel avulsion and trauma to tissue and internal organs.

The problem becomes acute when dissecting and harvesting blood vessels having a small diameter of about 3 to 8 mm. The techniques which are used for dissection of larger blood vessels such as the aorta are not applicable since the aorta is located in the retroperitoneum, bounded by the peritoneum on one side and the psoas muscle on the other side. An everting balloon placed in the infrarenal space located just below the kidney will track easily down the length of the aorta along a natural cleavage plane when inflated.

An everting type of balloon encounters difficulties when dissecting tissue adjacent a smaller-diameter vessel. This is due to the presence of less distinct planes that exist between small diameter blood vessels and the tissue that surrounds these vessels, as compared with the aorta and the tissue that surrounds the aorta. For example, if an everting balloon is placed adjacent to the saphenous vein in the leg, it usually skews dissection upon inflation rather than track along the vein. This is due to the amorphous nature of the fat and connective tissue that surrounds the saphenous vein.

Everting balloon catheters are known which are used for arterial dilation. (See, for example, U.S. Pat. No. 4,479,497 (Fogarty et al., Oct. 30, 1984) and U.S. Pat. No. 4,863,440 (Chin, Sep. 5, 1989)).

Double lumen everting balloon catheters, such as those disclosed in the Fogarty et al. '497 and the Chin '440 patents, have a through-lumen that slidably receives an endoscope. However, an endoscope used in conjunction with those disclosed catheters is unable to monitor the dissection process, since the endoscope lies within the central lumen proximal to the everting balloon. As the balloon everts from the catheter, the internal inflation pressure squeezes the walls of the balloon and closes off the distal viewing channel. Also, the area that requires monitoring during balloon dissection is located at the advancing front of the everting balloon. This area corresponds to the balloon/tissue interface that is subject to forces which cause tissue separation. Thus, an endoscope in the central lumen of existing double-lumen, everting balloon catheters is unable to view the area of tissue separation, since a double layer of balloon membrane lies between the endoscope and the tissue and blocks the endoscopic line of sight. This double layer obscures and distorts the viewing area of tissue separation.

Endoscopes have been disclosed for use in optical trocars such as in U.S. Pat. No. 5,385,572 (Nobles et al., Jan. 31, 1995) and EP 0 642 764 A1 (Sauer et al., published Mar. 15, 1995) and in harvesting blood vessels such as in U.S. Pat. No. 5,373,840 (Knighton, Dec. 20, 1994). The Nobles et al. '572 patent and the Sauer et al. '764 application disclose the use of sharp-tipped, metal cutting elements which extend outwardly from an endoscope positioned in the trocar. Control of the dissection is difficult because visualization of the vessel is obscured by the collapse of the tissue planes into the area between the cutting element and the endoscope. Furthermore, the risk of side vessel avulsion or trauma to the vessel is greatly increased by the orientation of the outwardly extending cutting elements.

The endoscope disclosed in Knighton '840 has a lateral dimension of a size sufficient to accommodate the blood vessel being harvested and at least one tool for use in harvesting the blood harvested. However, the failure of the endoscope to enlarge a cavity adjacent the blood vessel obscures viewing of the dissection area and manipulation of the vessel therein. The position of the viewing image relative to the tissue dissection area could obscure the identification of side vessels leading to an increased risk of vessel avulsion. Since the vessel is retrieved through the center of the endoscope, all side vessels must be severed for the endoscope to advance and the length of the vessel thus retrieved is limited substantially by the length of the body of the endoscope.

An instrument for penetrating body tissue, as disclosed in U.S. Pat. No. 5,271,380 (Riek, et al.), is equipped with a tapered tip of transparent material for viewing tissue penetrated by the tip using an optical unit which is positioned behind the tip. An instrument of this type may include a separate illumination channel that ends at the tip for illuminating tissue being penetrated.

SUMMARY OF THE INVENTION

The present invention provides a cannula for bluntly dissecting an elongated cavity in tissue particularly along the course of a vessel in a human or animal body. The cannula includes a tubular body having proximal closed end and distal blunt end and at least one lumen extending the length of the body. The cannula also includes an endoscope having a lighted, viewing end disposed in the lumen near the distal end of the body, and includes a transparent, tissue separating member, or blunt tip, substantially covering and selectively removable from the distal end of the body. The tissue separating member or blunt tip disposed on the distal end of the body includes internal walls that taper and end in a sharp point to reduce visual distortion through the endoscope that is optically aligned with the tip.

A method is also disclosed for bluntly dissecting an elongated cavity particularly along the course of a vessel using a cannula. The method includes the steps of: bluntly dissecting an initial cavity; separating the tissue by advancing the cannula along the cavity with continuous, visual observation; repeating the prior step of separating the tissue at least until the cavity is sufficiently elongated to advance a balloon therein; and successively inflating and deflating a balloon within the cavity to enlarge the cavity along the course of the vessel. Following dissection of the cavity along the vessel, a counterincision is made at the far end of the cavity, for example, to place a second blunt tip balloon trocar and to allow introduction of dissection instruments. The tip of the cannula is advanced out of the body through the counterincision, and the tapered tip is detached leaving the cannula body in the dissected cavity. The endoscope resides inside the cannula body, and the endoscope and cannula body are selectively positioned as a single unit inside the dissected cavity to facilitate isolating and harvesting the vessel. The method further may include removing the cannula, then maintaining the elongated cavity using insufflated gas through a balloon cannula that seals the incisions against gas leakage, or using a structural balloon, or a mechanical structural support within the dissected cavity.

In another embodiment of the present invention, the method includes the steps of bluntly dissecting an initial cavity; sealing and inflating the cavity; and separating the tissue along the cavity assisted by continuous, visual observation while under inflation until the cavity is sufficiently elongated.

The isolated vessel, such as the saphenous vein, may be harvested and removed for use as a coronary artery or peripheral vascular bypass graft, or may be left in place as an in-situ femoropopliteal or femoral-distal graft. The side branches of the vein are ligated, clipped, or occluded in both applications. In the case of an in-situ graft, the valves in the vein are disrupted by means of a valvulotome.

BRIEF DESCRIPTION OF THE DRAWINGS

FIGS. 8A AND 8B are partial side sectional views showing alternative embodiments of detachable blunt tips positioned at the distal end of the cannula;

FIGS. 9A AND 9B are pictorial side views showing, respectively, assembled and dissembled configurations of another alternative embodiment of the present invention;

FIG. 10 is a cross sectional view of cannula of FIGS. 9A and 9B;

FIGS. 11A, 11B and 11C are, respectively, side and sectional views of an alternate dissection probe that may be used with the cannula shown in FIGS. 9A and 9B;

FIGS. 11D and 11E are end views of the dissection probe in orbital positions about the cannula body;

DESCRIPTION OF THE PREFERRED EMBODIMENT

In accordance with one embodiment of the present invention, a cannula includes a tubular body having proximal closed end and distal blunt end, at least one lumen extending the length of the body, an endoscope having a lighted, viewing end disposed in the lumen near the distal end of the body, and a transparent, tissue separating member substantially covering the distal end of the body and selectively removable from the distal end. The present invention also includes methods for using such a cannula for separating tissue to form an elongated cavity along the course of a small blood vessel and subsequently harvesting the blood vessel, or using the blood vessel as an in-situ graft.

Figure 1:
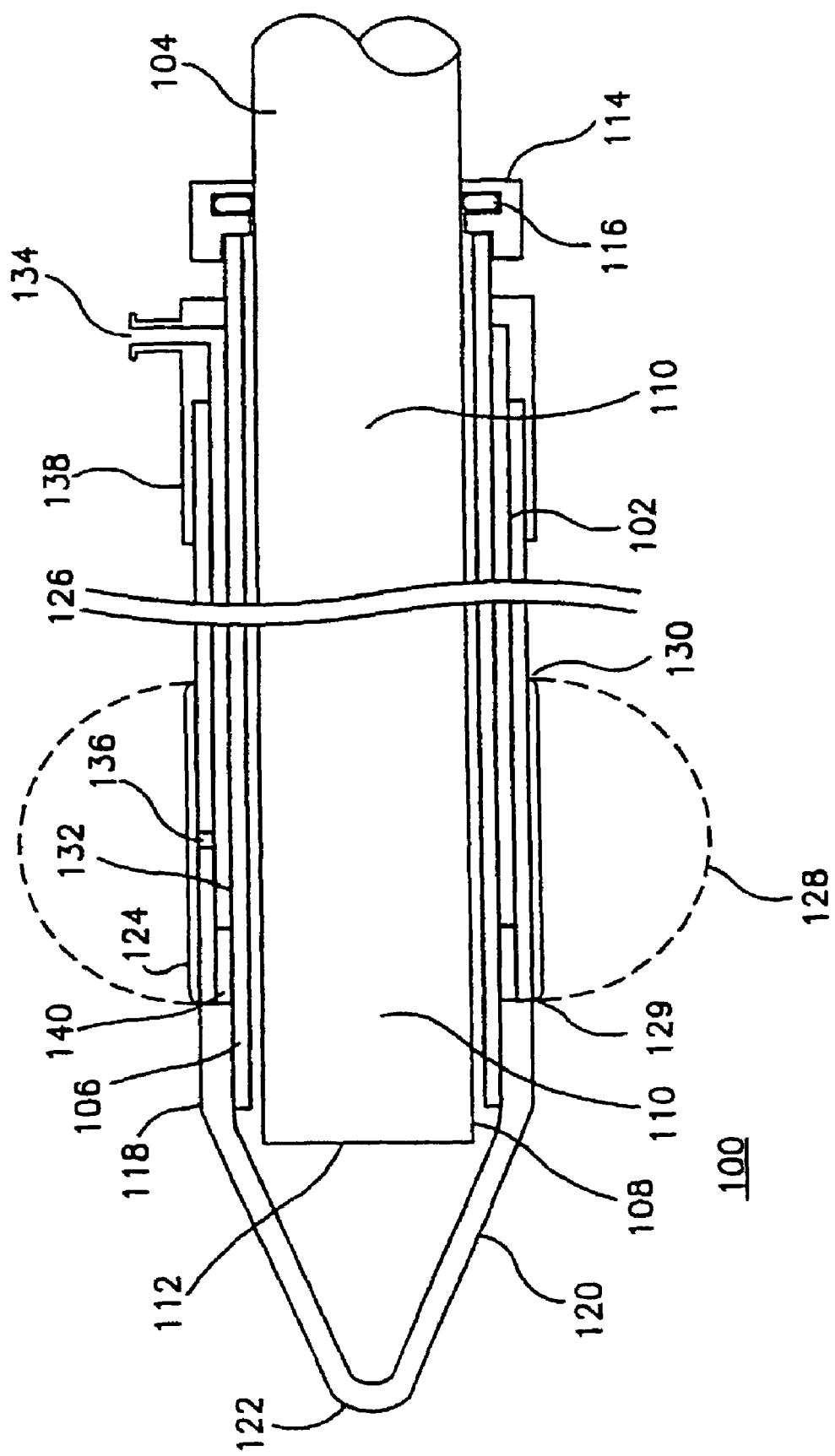
FIG. 1 is a partial, longitudinal cross-sectional view of a cannula of the present invention illustrating the profile of a tissue separating member affixed thereto.

FIG. 1 shows an embodiment of the cannula 100 of the present invention. The cannula 100 includes a tubular body 102 having a proximal end 104 and a distal end 106. At least one lumen 108 extends the length of the body 102. Disposed in the lumen 108 is an endoscope 110 having a lighted, viewing end 112 near the distal end 106 of the body. The other end of the cannula 100 has a proximal end cap 114 and an elastomeric washer 116 that provides a pressure-sealed, sliding fit with the endoscope 110.

The cannula 100 also includes a transparent, tissue separating member or blunt tip 118 substantially covering the distal end 106 of the body. The tissue separating member 118 has a tapered section 120 which angles toward a blunt, tissue-separating tip 122 distal to the distal end 106 of the tubular body. The shape of the tissue separating member 118 allows atraumatic dissection of a cavity with sufficient control and maneuverability to prevent tearing or puncturing of the nearby vessel. Typically, the tip 122 has an outer radius of curvature of about 0.030" to about 0.100", and preferably of about 0.045". The length of the tapered section 120 of the tip is approximately 0.500" in length. The tapered shape and blunt tip of the tissue separating member 118 thus allows deflection of branch vessels to the side of the cannula 100 without their avulsion, upon forward advancement of the cannula 100 with reduced requirement of applied axial force to advance the cannula and tip through tissue being dissected.

In tapers of uniform wall thickness with a rounded inner surface near the apex, it has been found that a small circular spot of distortion exists in the center of the visual field of the endoscope, equivalent to the diameter of the rounded taper tip. This distortion may be substantially eliminated by forming the transparent taper with an inner profile that ends in a sharp point, or apex, while maintaining the outer profile as a rounded tip with approximately a 0.045" radius. Undistorted visual imaging through such tip thus allows the surgeon to track down the vessel, identify side branches, and guide the device past the side branches. An optimal taper length of approximately 0.5" facilitates cannula manipulation around side branches, and the preferred configuration of the tapered tip is illustrated in FIGS. 8A and 8B.

Figure 2:
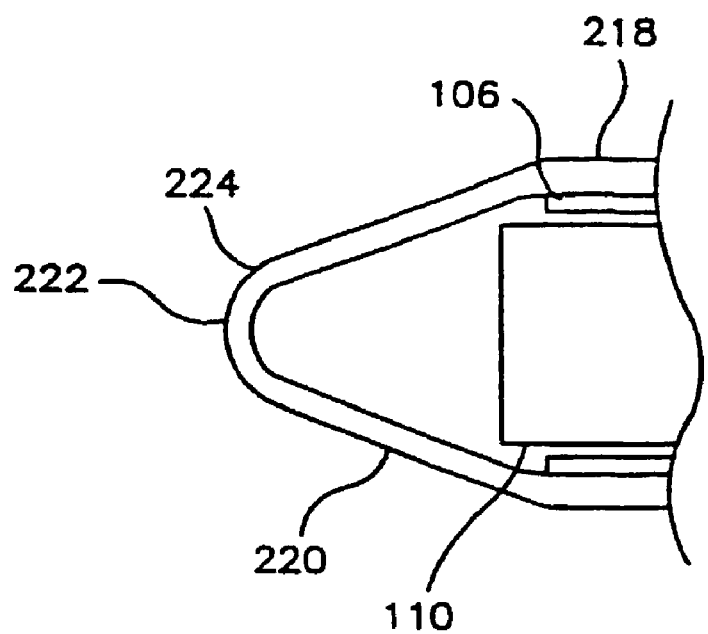
FIG. 2 is an isolated, cross-sectional view of another embodiment of the tissue separating member having a blunt spherical tip with a straight tapered section suitable for use with the cannula of the present invention.

Alternative embodiments of the present invention include other shapes for the tissue separating member 118 which provide the necessary control and atraumatic dissection. FIG. 2 illustrates another embodiment of a tissue separating member 218 which substantially covers the distal end 106 of the cannula and provides a transparent shield for the endoscope 110. The tissue separating member 218 includes a tapered section 220 integrally formed with a more blunt, spherical section 224 at the distal tip 222 of the tissue separating member.

Figure 3:
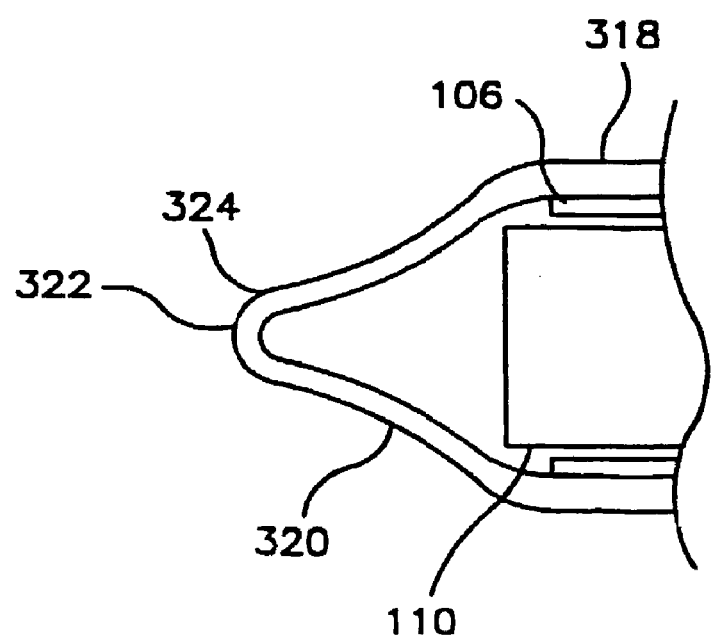
FIG. 3 is an isolated, cross-sectional view of another embodiment of the tissue separating member having a blunt tip with a curved tapered section suitable for use with the cannula of the present invention.

FIG. 3 illustrates another embodiment of a tissue separating member 318 which substantially covers the distal end 106 of the cannula and provides a transparent shield for the endoscope 110. The tissue separating member 318 includes a curved tapered section 320 integrally formed with a blunt section 324 at the distal tip 322 to form a duck-bill shape. The curved tapered section 320 can have convex or concave shape.

Figure 4:
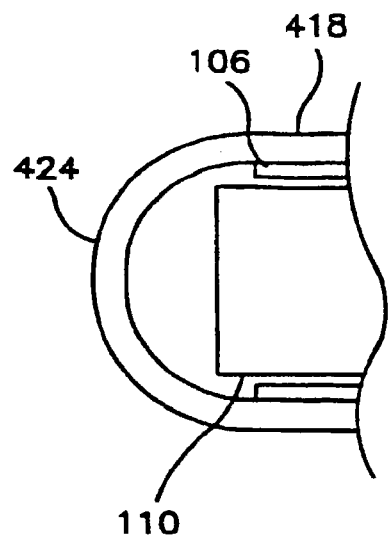
FIG. 4 is an isolated, cross-sectional view of another embodiment of the tissue separating member having a hemispherical shape suitable for use with the cannula of the present invention.

FIG. 4 illustrates another embodiment of a tissue separating member 418 which substantially covers the distal end 106 of the cannula and provides a transparent shield for the endoscope 110. The tissue separating member 418 has a hemispherical shape 424 covering the distal end 106.

Preferably, the tissue separating members 118, 218 have an overall length of about 0.5 inches and a uniform wall thickness of about 0.06 inches along the entire surface to allow visualization by the endoscope without distortion of the image that would result if a section of the wall is thickened or otherwise forms a lens. The wall thickness of the tissue separating member may be contoured to form a lens for special applications that require a magnified or otherwise distorted image, e.g. asymmetric, fish-eyed image, or the like, transmitted by the endoscope. Suitable materials for making the tissue separating member or blunt tip include polycarbonate and any material which is sufficiently strong to separate tissue and sufficiently transparent to allow visualization by the endoscope. As illustrated in FIGS. 8A, 8B, 9A, and 9B, the tissue separating member or blunt tip may be attached by threads or bayonet-type twist lock to the cannula for selective removal during procedures later described herein.

Referring again to FIG. 1, the cannula 100 preferably includes a balloon 124 located at the distal end 106 on the exterior wall 126 of the cannula. The balloon 124 may be elastic or inelastic, although an elastomeric balloon is preferred because it achieves a smaller, smoother outer profile. Fully inflated (as shown in phantom 128 in FIGS. 1, 8A, and 8B), the diameter of the balloon 124 is about 3 cm. Preferably, a sleeve type of balloon 124 has both the distal end 129 and proximal end 130 of the balloon secured to the exterior wall 126 of the cannula.

The balloon 124 is selectively inflated by supplying thereto via another lumen 132 a pressurized fluid, such as a gas or liquid, from an inflation port 134 to a hole 136 in the exterior wall 126 of the cannula between the proximal and distal ends 129, 130 of the balloon to communicate with the interior thereof. A plunger device, such as a manually-operated syringe, is suitable for connecting at the inflation port 134 to control the inflation of the balloon 124. The lumen 132 is formed as another tubular body 138 in a concentric arrangement with the body 102 to form a space 140 between the two bodies. Another embodiment suitable of the present invention may include two lumens 108, 132 in a side-by-side arrangement. Additional lumens can be added in similar manner to provide other functions such as irrigation and aspiration in known manner.

The present invention is illustrated using a sleeve type of balloon with the cannula 100. Other balloon types are suitable for use with the present invention such as, and not limited to, using an invertable balloon positioned in a separate lumen in the cannula to assist in separating the tissue when inflated.

The cannula 100 may be manufactured from a variety of bioinert, substantially inelastic materials, such as stainless steel, polyethylene, polyurethane, polyvinyl chloride, polyimide plastic, and the like that preferably have a tensile strength of at least 10,000 psi. Preferably, each lumen of the cannula 100 has a wall thickness of between about 0.005 inch and 0.010 inch.

The endoscope 110 has an outer diameter of approximately 5.0 mm and an endoscope may be permanently built into the cannula 100, or may be a separate device that is advanced through the endoscope lumen 108, for example, through a sliding gas-tight seal 805 configured as shown in FIG. 8A in conventional manner. The endoscope 110 is positioned within the lumen 108 with the tip in correct position to allow unimpeded visualization through the transparent blunt tip of the surrounding tissue and vessel outside of the cannula 100. A preferred endoscope 110 having a tubular diameter of about 5.0 mm is commercially available from Solos Endoscopy, Inc., at Norcross, Ga., although other commercially-available endoscopes 110 as small as 1.00 to 1.75 mm in diameter may also be used.

Figures 5, 6:
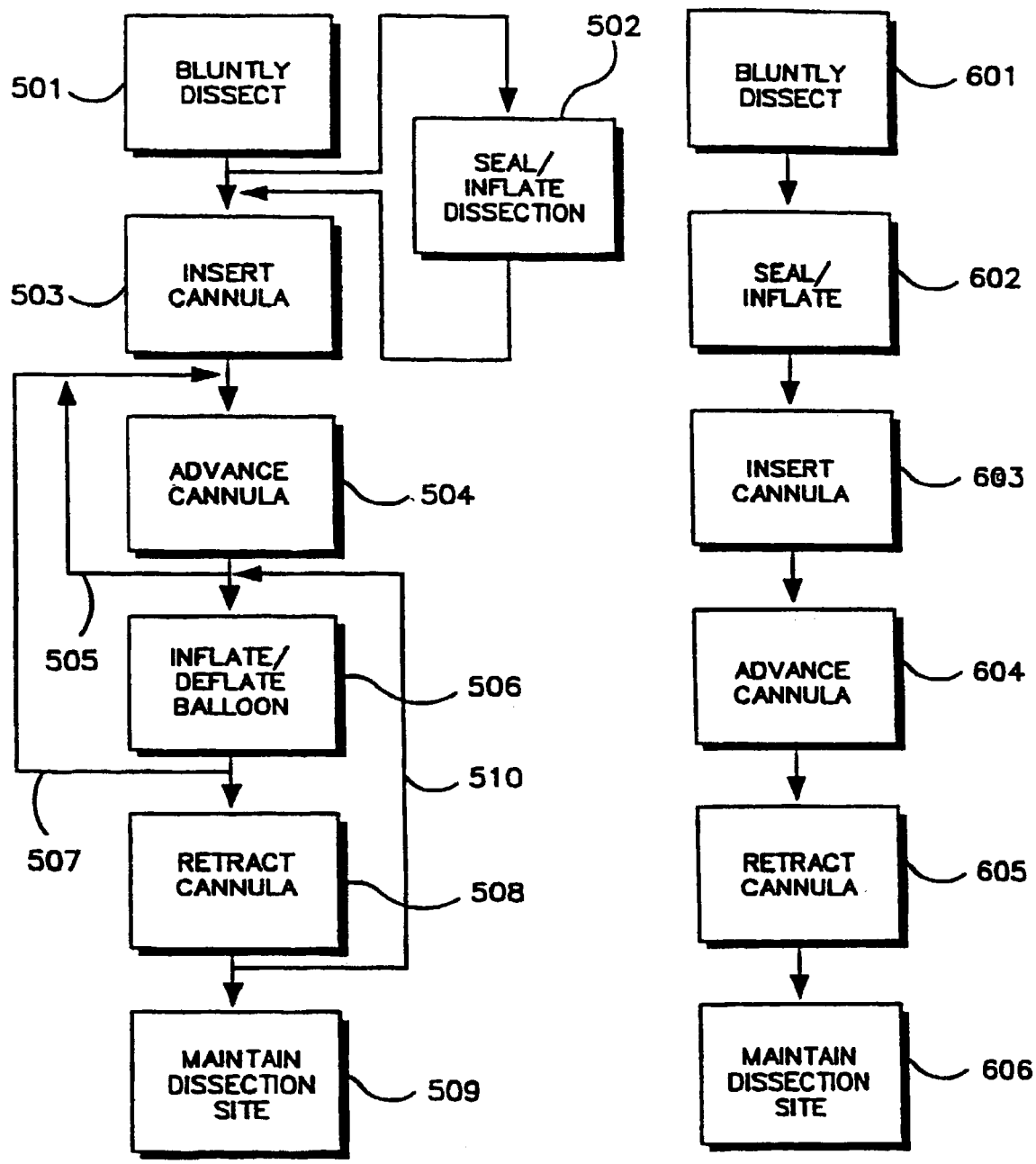
FIG. 5 is a flowchart of one embodiment of the method of separating tissue using the cannula of the present invention.
FIG. 6 is a flowchart of another embodiment of the method of the separating tissue.

Methods for bluntly dissecting an elongated cavity using the cannula of the present invention are shown in the flow diagrams of FIGS. 5 and 6. Although the blunt dissection of an elongated cavity along the course of a vessel is specifically described, the present invention is generally suitable for separating any tissue. For example, the cannula may be used to track along the median nerve from an incision at the patient's wrist, forming a cavity for surgical treatment of carpal tunnel syndrome. The cannula allows visualization and tracking of the median nerve, preventing the injury to the nerve which may occur if blind advancement of a balloon cannula were used. Alternatively, the cannula of the present invention may also be used to dissect a cavity adjacent the mammary artery in the manner as later described herein.

The method illustrated in the flow diagram of FIG. 5 includes the steps of incising the skin and bluntly dissecting 501 through the subcutaneous tissue to the level of the selected vessel or nerve. Blunt dissection is performed to separate the vessel from adjacent tissue for a length of approximately 1 to 2 cm. The blunt dissection may be performed with a pair of curved Metzenbaum scissors, using the tips of the scissors to cut and bluntly spread tissue in a plane between the vessel and the adjacent tissue.

Preferably, a blunt tip balloon cannula is introduced into the space between the vessel and the overlying tissue. The balloon is then inflated to form a gastight seal which seals 502 the dissection. A gas such as carbon dioxide is infused under pressure via another lumen in the cannula having an external opening positioned distal to the balloon. The natural perivascular plane around the vessel is expanded by the injected gas, forming a tract along the course of the vessel. For a superficial vessel such as the saphenous vein, the expanded tract is visible on the surface of the skin. The interior of the expanded tract is not cleanly open but rather, includes gossamer-like strands of connective tissue and fat, preventing unobstructed visualization and making hazardous the passage of an endoscope along the tract adjacent to the vessel. If a conventional endoscope is pushed into this connective tissue in an attempt to form a cavity adjacent to the vessel, the view through the conventional endoscope is blurred by the tissue that contacts the viewing end of the conventional endoscope. A blurred view through the conventional endoscope increases the potential for side branch avulsion during blunt dissection of the perivascular tunnel.

The cannula 100 is inserted 503 into this dissected space. With the fiberoptic endoscope 110 continuously visualizing down the course of the vessel, the cannula 100 separates the tissue by advancing forward 504, probing between the vessel and the adjacent gossamer perivascular tissue in the plane initiated by blunt dissection. The transparent, tissue separating member 118 allows the endoscope 110 to clearly visualize a segment of the vessel at least equivalent to the length of the tapered section 120.

If the blunt dissection along the course of the vessel is not sufficient to advance the balloon 124 therein, the method returns 505 to the step of advancing the cannula 504 forward to continue the separation of tissue along the course of the vessel. When a cavity of sufficient length has been formed by the cannula 100, the balloon 124 is successively inflated and deflated 506 to enlarge the cavity to about 3 cm in diameter.

The method returns 507 to the step of separating the tissue by advancing the cannula 504 and the step of selectively inflating and deflating 506 the balloon 124, as described above. Successive application of these steps forms a cavity along the entire length of the vessel. Once the elongated cavity is complete, the cannula 100 is completely retracted 508 from the elongated cavity.

The elongated cavity site is then maintained 509 in expanded form in accordance with the method of the present invention. Following use of the cannula 100 to form an elongated cavity along the course of a vessel, the cavity must be supported to allow procedures to be performed on the vessel, such as vessel dissection, grafting of the vessel, or vessel harvesting. A blunt tip trocar may be used to seal the entrance incision and allow gas insufflation to maintain the cavity in expanded form. One blunt-tip balloon trocar suitable for use herein is presently marketed by Origin Medsystems, Inc. of Menlo Park, Calif.

Another method of maintaining the cavity in expanded form includes making an incision at the distal extent of the dissected cavity, and inserting a double rod system through the cavity. The double rods are suspended via a laparoscopic mechanical lifting device to maintain the cavity. This system allows instruments to be advanced into the cavity via simple incisions, without the requirement for trocars with gas sealing valves, as is the case with gas insufflation.

Alternatively, an inflatable structural balloon or mechanical structure may be used to support the dissected cavity. For example, the cavity may be maintained by mechanical retraction or by a mechanical finger-like retractor attached to a powered lifting arm plus a separate flat balloon retractor used to displace the side wall of the cavity. The endoscope 110 may be introduced behind the legs of the finger-like retractor that connect to the mechanical lifting arm.

The vessel is completely dissected within the formed cavity, using laparoscopic instruments such as graspers, scissors, hooks, and blunt probes. Side branches to the vessel may be ligated using suture ties, clipped using titanium vessel clips, cauterized using electrocautery, or a combination of these procedures. The dissected vessel is removed from the cavity for possible use as a conduit for an arterial bypass procedure, or the vessel may be left in place to be used as an in-situ bypass graft.

In an alternate embodiment, the method of the present invention forms a small diameter cavity, about 7 mm, along the entire length of the vessel before the cavity is then enlarged. As illustrated in FIG. 5, the steps of making a blunt dissection 501, sealing and inflating the dissection 502, inserting 503 the dissection cannula 100 and successively separating the tissue by advancing 504 the cannula 100 are performed as described above. The alternate method, however, continues advancing 504 the dissection cannula until the entire length of the elongated cavity is bluntly dissected to the small diameter of about 7 mm.

Only after the entire length of the elongated cavity has been bluntly dissected does the alternate method include the step of inflating and deflating 506 the balloon 124 of the cannula to increase the diameter of the distal end of the elongated cavity to about 3 cm. The dissection cannula 100 is then retracted 508 partially by about the length of the balloon 124. The alternate method then returns 510 to the steps of inflating and deflating 506 the balloon 124. The cannula 100 is again retracted 508 partially and the method returns 510 to repeating the above steps until the entire length of the elongated cavity has been enlarged to the diameter of the inflated balloon 124 which is typically about 3 cm.

An alternate method involves making an incision down to the vessel. Blunt dissection of the vessel from the adjacent tissue is performed for a 3-4 cm length. A blunt tip trocar is placed in the incision, and gas insufflation is initiated.

The cannula 100 is inserted through the blunt tip trocar, and blunt dissection using the balloon 124 is performed under the presence of gas insufflation in the cavity. This technique provides a larger cavity for visualization during separation of the tissue, since gas insufflation is used from the onset of blunt dissection. However, a gas sealing blunt tip trocar is required. If vessel dissection without gas insufflation is conducted, and a double rod system is used to maintain the cavity, then the use of a blunt tip trocar may be avoided.

Another method of the present invention forms a small diameter cavity along the entire length of the vessel. The cavity is enlarged only by the initial inflation at the blunt dissection site. As illustrated in FIG. 6, the steps of making a blunt dissection 601, sealing and inflating the dissection 602, inserting 603 the cannula 100, and successively separating the tissue by advancing 604 the cannula 100 are performed as described above. The cannula advances 604 until the entire length of the elongated cavity is bluntly dissected and expanded only by the inflating gas of the prior step 602. The cannula 100 is then retracted 605 entirely from the elongated cavity. The dissection site is maintained 606 in expanded form as described above.

The present invention includes methods particularly useful for harvesting vein. In one method, an incision is made near the ankle, and the cannula is passed along the saphenous vein up to the knee, or near the knee. Following balloon inflation to enlarge this segment, an incision is made into the dilated cavity near its endpoint at the knee. The incision at the knee is the approximate mid-point of the saphenous vein between the ankle and the groin. The vein is isolated and the side branches ligated in this segment between the ankle and the knee to harvest and remove this segment.

The segment from the knee to the groin is then harvested. The cannula may be passed from the same knee incision used for harvesting the vein from the lower leg, or a separate incision down to the vein may be made slightly above the knee. Use of a separate incision may be useful if the vein is overly curved or tortuous as it passes around the knee. The cannula is advanced toward the groin, the balloon is inflated to dilate the cavity, an incision is made into the dilated cavity at its groin end, and the portion of the saphenous vein residing in the thigh is harvested.

As an alternate method for saphenous vein harvesting, the initial incision may be made at the knee. The cannula is passed successively in both directions, toward the ankle and toward the groin, from the same incision. Then additional incisions are made at the ankle and at the groin to allow harvesting of the entire length of the saphenous vein. The vein may be removed as a single strand, or it may be cut at the knee and removed as two strands.

In some anatomic regions, it may be difficult to advance a rigid, straight tissue separation device along the course of a vessel. For example and referring to FIG. 7, if the saphenous vein 700 is harvested by passing the cannula 702 from an incision 712 just above the ankle, the presence of the medial malleolus 704 and the foot 706 may prevent an otherwise rigid cannula from being angled upwards or sideways to follow the vein 700.

Figure 7:
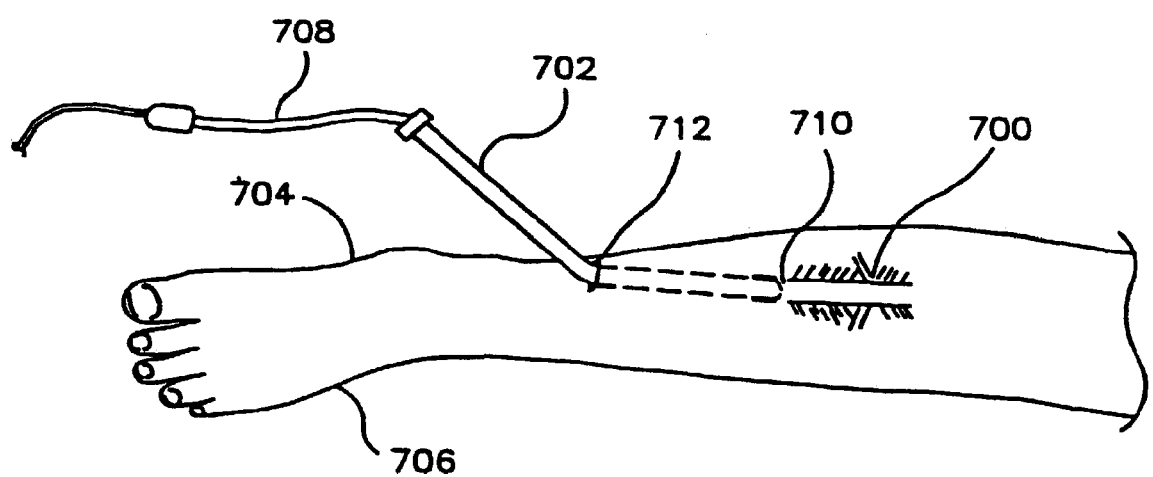
FIG. 7 is a partial side view of a patient's leg with the advancement of a flexible cannula of the present invention through an incision.

For such obstructed situations, the cannula 702 may be formed with a body which is flexible or otherwise malleable, or is rigid with a pre-determined gradual arc, as shown in FIG. 7. The endoscope 708 that is inserted into the cannula 702 up to the tissue separating member 710 must also be flexible to facilitate shaping the flexible body within the curved cannula. Such conventional flexible fiberoptic endoscopes are commercially available for use in gastrointestinal endoscopy.

In other embodiments of the method, and of the apparatus illustrated in FIGS. 8A and 8B, the tapered and transparent tip 803 of the cannula 800 may be removably attached to the body of the cannula. At the cannula insertion site, a blunt tip balloon trocar (for example, as commercially available from Origin Medsystems, Inc.) is placed to seal an incision and allow insufflation into the space to be dissected by the cannula 800 which is advanced through the blunt tip trocar along the course of the vessel. The balloon on the cannula is selectively inflated to dissect a perivascular cavity. Following dissection of the cavity along the vessel, a counterincision is made at the far end of the cavity to place a second blunt tip balloon trocar and allow introduction of dissection instruments. The tip of the cannula is advanced out of the body through the counter-incision and the tapered tip 803 is detached, leaving the cannula body in the dissected cavity. The endoscope resides inside the cannula body, and the endoscope/cannula body is advanced as a single unit inside the working cavity to isolate and harvest the vessel.

The detachable tip 803 may be attached to the cannula body 800 using a threaded connection between the tip and the distal end of the cannula body, or a bayonet-type of fitting my be used to lock the tip onto the cannula, with a slot in the tip engaging a pin on the end of the cannula body.

The cannula of this embodiment with a detachable tip 803 has the advantages compared with the embodiment of the cannula described with reference to FIG. 1 that the 5 mm diameter endoscope used with the cannula often does not have sufficient rigidity to allow it to be directed along the dissected working cavity for unobstructed visualization. For example, in the lower leg, the curvature of the calf muscle impedes visualization along the surgical cavity, and the endoscope must deflect muscle tissue to allow it to view down the bore of the cavity. Flexion of the endoscope which is about 45 cm long and about 5 mm diameter may prevent successful visualization. The cannula which surrounds the endoscope according to the present invention has an 8 mm outer diameter, and this larger diameter imparts rigidity to the endoscope/cannula system. The cannula body may be constructed of stainless steel for additional rigidity.

Also, the ability to remove the tapered tip 803 via an incision at the opposite end of the cavity results in a decreased number of passes of the cannula and endoscope up and down the length of the cavity. This adds to the convenience of the procedure, and decreases the potential for vessel injury by decreasing the number of full length passes required through the dissected cavity.

Referring now to FIGS. 9A and 9B, retracted and dissembled configurations of another embodiment of the cannula 900 of the present invention are illustrated. Specifically, the outer body of the cannula 900 includes a sleeve-type balloon 901 secured to the body at proximal and distal ends thereof, as illustrated in FIGS. 8A and 8B, for selective inflation via a lumen 1010 within the body that communicates therewith, as illustrated in the sectional view of FIG. 10.

At the distal end of the body of the cannula 900, a detachable, transparent blunt tip 903 is shown in FIG. 9A retracted onto the distal end of the cannula body, and is shown in FIG. 9B mounted on push rod 906 and extended beyond the distal end of the cannula body 900 to expose the viewing end 905 of an endoscope, and a crescent-shaped dissection probe 907. The probe 907 is mounted on shaft 909 to facilitate selective manipulation of the dissection probe 907 within the field of view of the endoscope 905. As shown in FIG. 10, the push rod 906 may be non-circular within a mating non-circular lumen to retain the blunt-tip 83 in axial alignment as it is selectively extended and retracted relative to the distal end of the cannula body 900. Also as shown in FIG. 10, the shaft 909 for supporting the dissection probe 907 may be circular or cylindrical to facilitate both longitudinal and rotational positioning of the dissection probe 907 via corresponding manipulations of the shaft 909 at the proximal end of the cannula body 900. Alternatively, the shafts 906 and 909 may reside in slots of suitable sectional shapes along the outer surface of the cannula body 900, with an encircling sheath of heat-shrinkable PET plastic, or other bioinert plastic, to retain the shafts 906, 909 in captivated orientation along the cannula body 900.

The dissection probe 907 has leading and trailing edges thereof to facilitate selective dissection of strands of connective tissue and lateral branch vessels along the saphenous vein, or other vessel, to be harvested. The blunt tip 903 may thus be selectively extended beyond the cannula body 903 (or the cannula body 900 may be retracted relative to the tip 903) to expose the dissection probe 907 at a selected location along a dissected cavity adjacent a vessel being harvested. Selective translational and rotational manipulations may be achieved via similar manipulations of the shaft 909 at the proximal end thereof to dissect connective tissues and lateral branch vessels along the course of the vessel being harvested. The dissection probe 907 and the blunt tip 903 may then be retracted into axial alignment with the cannula body 900, as shown in the retracted configuration of FIG. 9A. Surgical procedures involving the cannula 900 of FIG. 9A are described later herein with reference to the flow chart of FIG. 16.

Referring to the side and sectional views of FIGS. 11A, 11B, and 11C, the dissection probe may be formed in separate, spiral-like segments 1101, 1103 that are axially spaced along the supporting shaft 909, for example, in the illustrated configuration, to provide greater convenience in selectively bypassing or dissecting connective tissue and lateral branch vessels along the course of a vessel being harvested. Thus, as shown in FIGS. 11D and 11E, the dissection probe 907 (or 1101 and 1103) may be orbited about the axis of shaft 909, and the cannula body 900 may be rotated on its longitudinal axis to facilitate the dissection of the vessel away from connecting tissue, and the traversal of side-branch vessels.

Figure 12A:
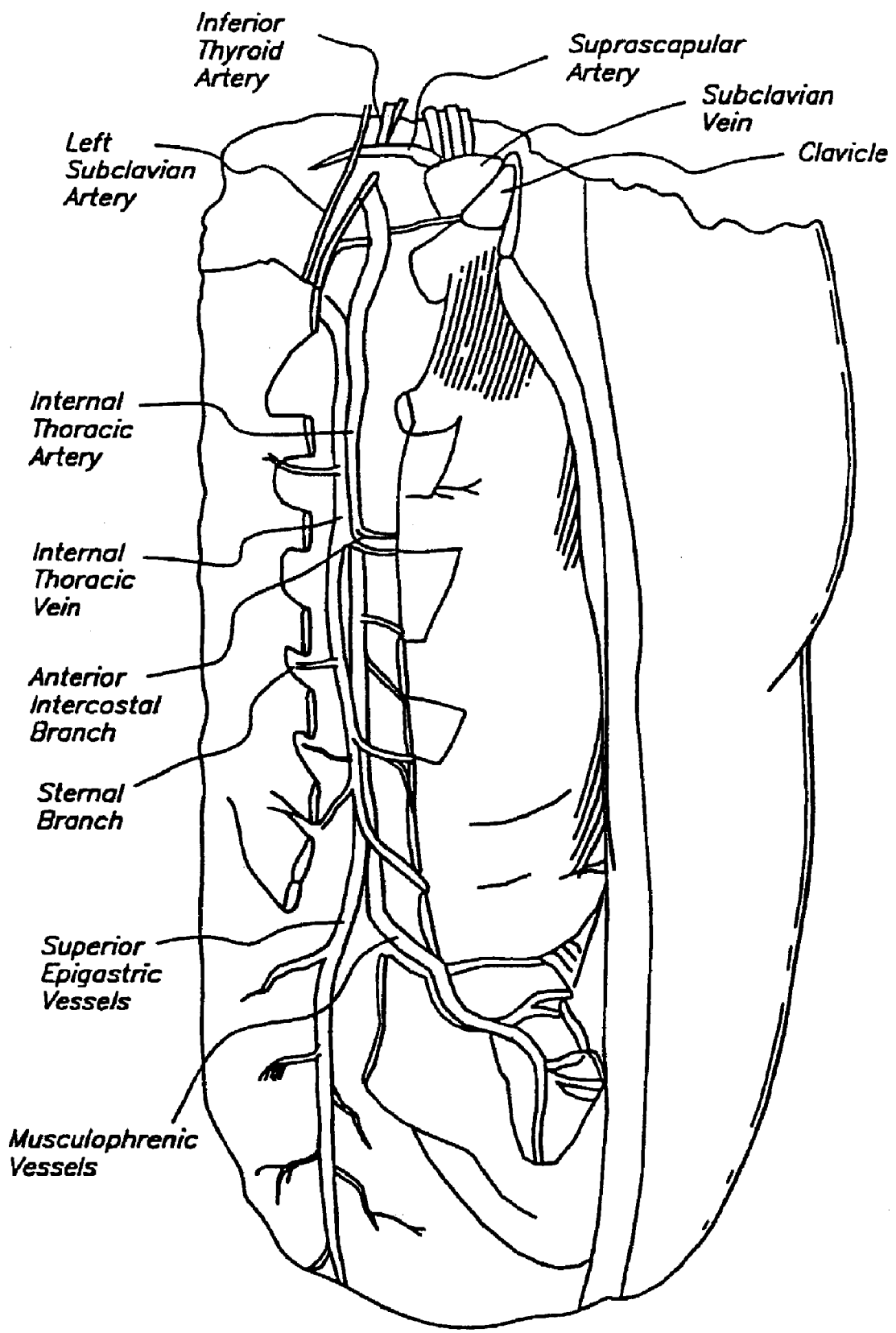
FIGS. 12A, 12B and 12C are, respectively, simplified anatomical side sectional and front sectional views of the human body.
Figure 12B:
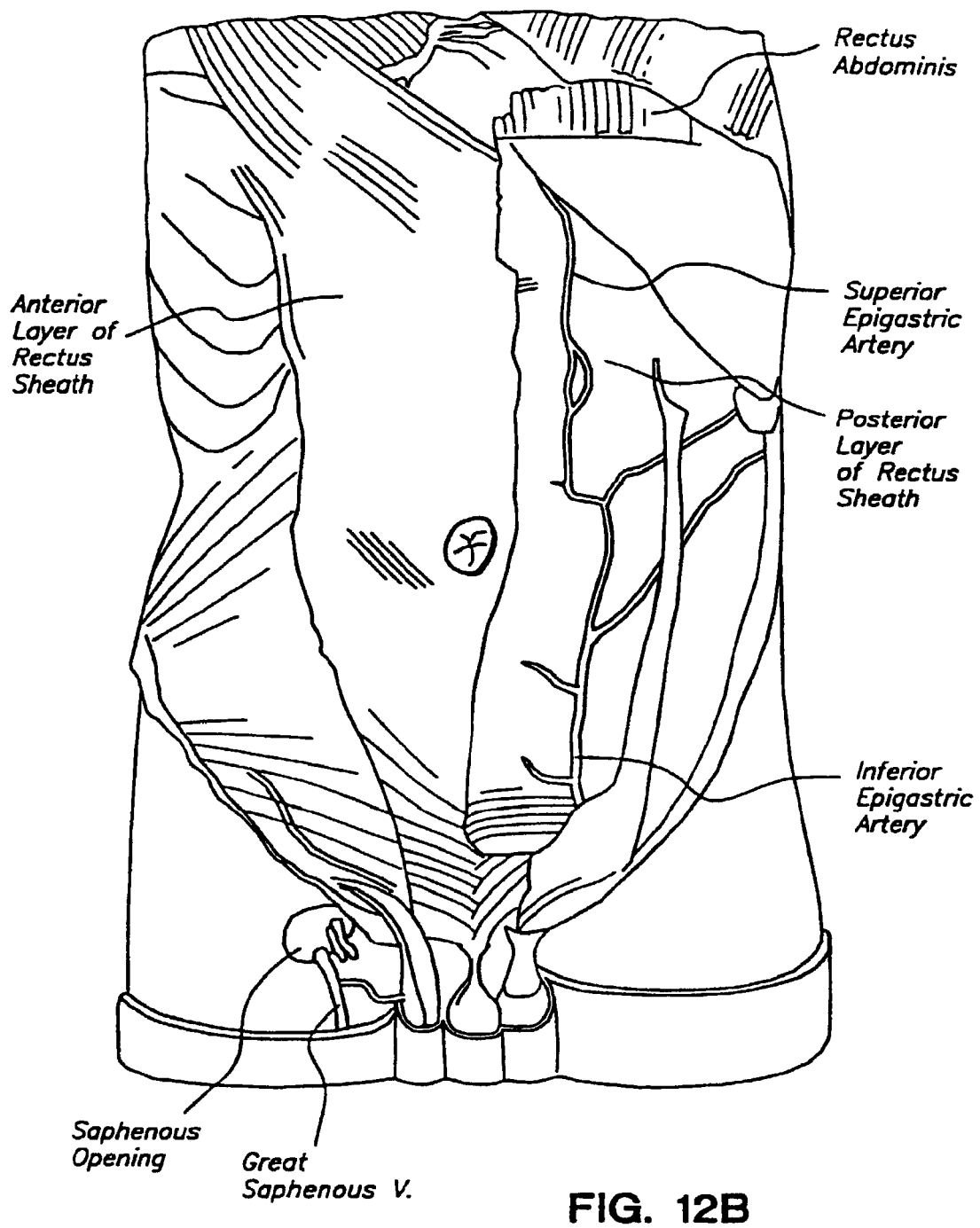

Referring now to FIGS. 12A and 12B, the simplified side and frontal illustrations of the human anatomy disclose another operating environment for the apparatus and method of the present invention, for example, in preparing the internal mammary artery for coronary artery bypass. Specifically, the combined blunt tip cannula and dissection probe of the present invention permits a working cavity to be formed along a vessel, and the vessel to be dissected and isolated, or otherwise manipulated as later described herein, via a single incision. This decreases the number of incisions required to harvest a vessel. The cannula and dissection probe of the present invention facilitate harvesting the internal mammary artery in the chest wall to enable its use as a coronary artery bypass graft. The internal mammary artery may be harvested via a single subxiphoid incision, with the rectus muscle bluntly dissected to expose the superior epigastric artery. The cannula tracks along the superior epigastric artery which leads directly to the internal mammary artery that lies behind the ribs lateral to the sternum. The internal mammary artery is dissected substantially in the manner as previously described up to its origin at the subclavian artery. Its side branches are clipped and transected, and distally, it is transected to yield a free end which is anastomosed to the coronary artery to complete the bypass.

Figure 12C:
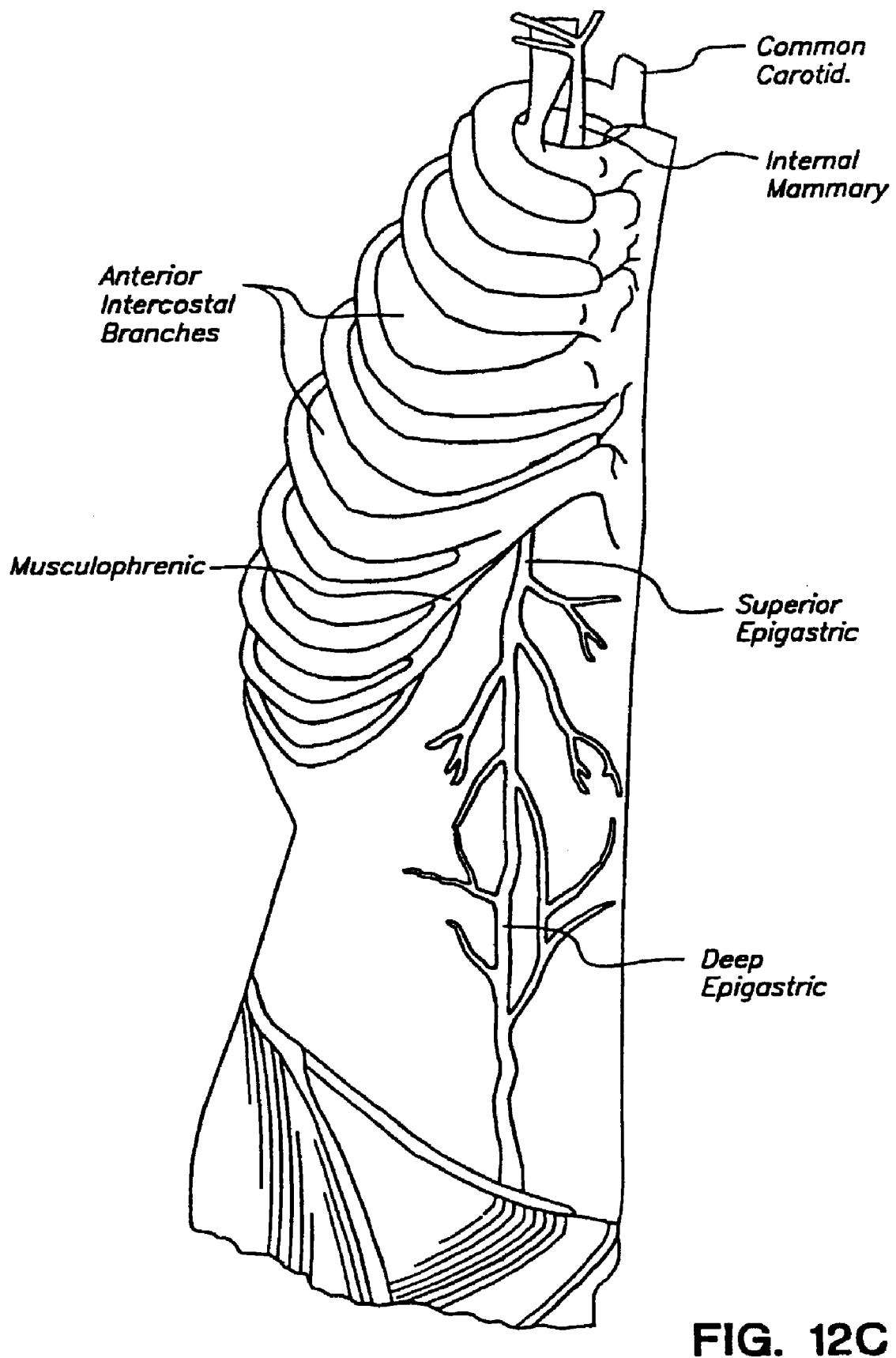

As illustrated in FIGS. 12A, 12B and 12C, the internal mammary artery (also known as the internal thoracic artery) runs internal to the costal cartilages, lateral to the sternum, descending to the interval between the sixth and seventh cartilages where it bifurcates into the superior epigastric artery and the musculophrenic artery. The superior epigastric artery lies within the rectus sheath. In its superior portion, it lies behind the rectus abdominis muscle. The superior epigastric artery eventually anastomoses with the inferior epigastric artery.

Since the superior epigastric artery lies in the abdominal wall within the rectus sheath, it may be easily found, for example, using Doppler ultrasound, and isolated via incision of the skin and blunt spreading of the rectus abdominis muscle overlying the artery. The blunt tip, visual balloon dissection cannula previously described herein may be placed next to the isolated section of superior epigastric artery, and passed superiorly, following the course of the superior epigastric artery to its junction with the internal mammary artery. An endoscopic working cavity may be formed along the length of the internal mammary artery in the manner previously described herein, allowing side branch identification and interruption, and using vessel clips or bipolar electrocautery closure followed by scissor transection. The dissected portion of the internal mammary artery may then be used to revascularize diseased coronary arteries, facilitated by the availability of the endoscopic working cavity thus formed along the internal mammary artery.

This abdominal approach to internal mammary artery dissection is preferable to a supraclavicular approach or an intercostal approach since the supraclavicular approach is impeded by the presence of the subclavian artery and the aortic arch, and dissection risks trauma to these vessels. In contrast, the intercostal approach gives limited exposure, unless rib spreaders are used, and only a small portion of the internal mammary artery is accessible from the side. The abdominal approach described herein thus allows the entire length of the internal mammary artery to be exposed. By initiating the dissection at the level of the superior epigastric artery, no vascular or bony structures are present to impede the passage of the dissection cannula of the present invention, thereby resulting in a safer approach to the internal mammary artery.

Figure 15:
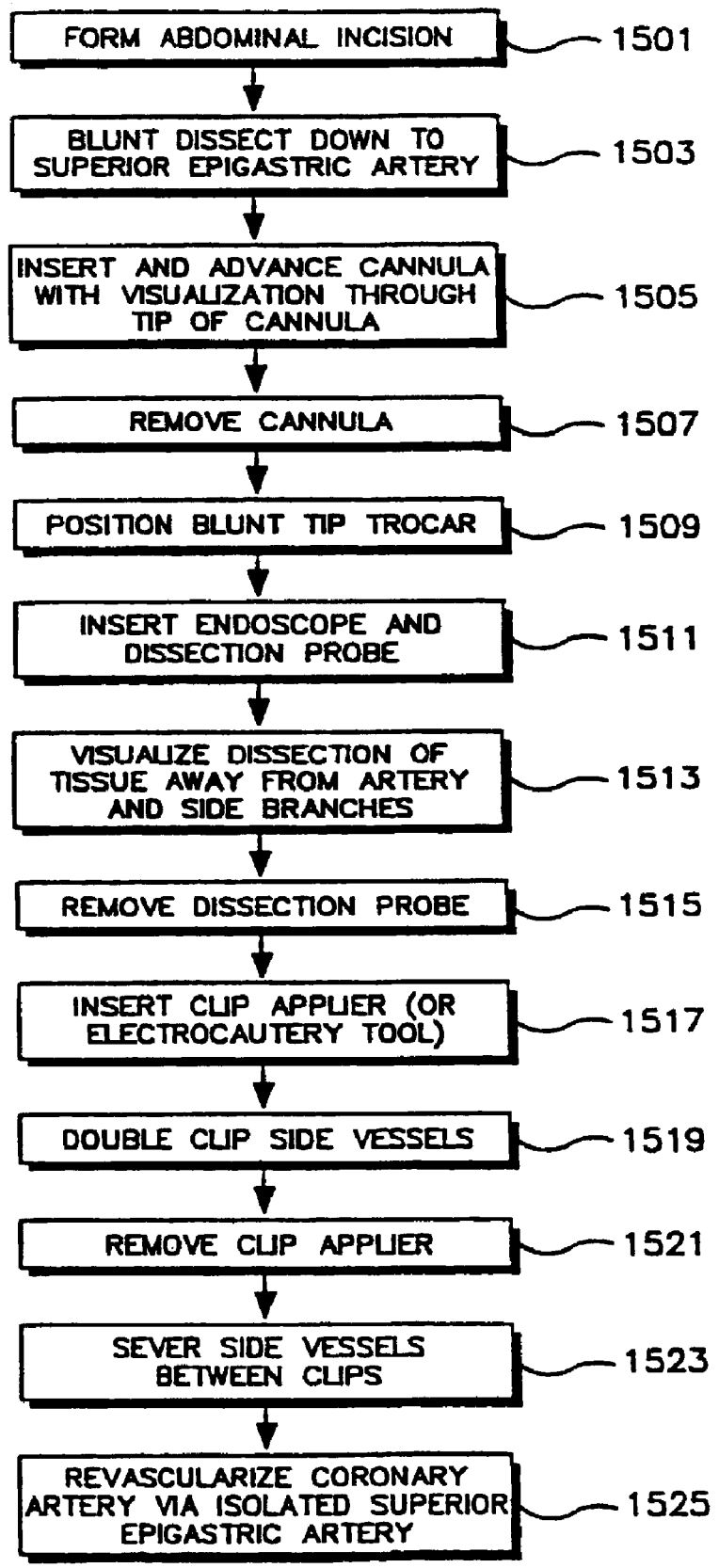
FIG. 15 is a flow chart of an artery isolating procedure according to the present invention.

Specifically, with reference to the flow chart of FIG. 15, the method of creating a working space along the superior epigastric artery according to the present invention includes forming an incision 1501 of the skin and blunt dissection 1503 and spreading of the rectus abdominus muscle overlying the artery. The balloon cannula as illustrated in FIG. 1, or 8A, 8B, or 9A, 9B, 13A, 13B is inserted in the bluntly dissected cavity next to the isolated section of the superior epigastric artery. The cannula is advanced 1505 along the course of the superior epigastric artery and the internal mammary artery by the iterative sequence of advancing the cannula, visualizing dissection of tissue through the transparent tip until resistance to tissue penetration is felt. The balloon is inflated to expand the cavity around the cannula adjacent the artery, and then deflated, and the cannula is again advanced, and retracted and diverted and advanced as required to properly track the course of the vessel substantially to its junction with the subclavian artery. The tunnel or cavity thus formed along the artery facilitates side branch identifications for subsequent operative procedures, and in one embodiment of the process invention the cannula may be completely removed 1507 from the working cavity thus formed by successively inflating and deflating the balloon to establish an adequate working cavity as the cannula is completely withdrawn therefrom.

Next, the artery may be dissected from the cavity wall by placing 1509 a blunt tip trocar in the working cavity at the abdominal incision, and the associated balloon is then inflated. The cannula of the present invention including the dissection probe and an endoscope positioned 1511 within a lumen of the cannula is positioned in the working cavity through a gas tight port of the trocar, with the dissection probe positioned about the artery. The dissection probe is now translated and rotated 1513, as illustrated in FIGS. 11D and 11E to free the artery from connective tissue. The axial opening 908 in the perimeter of the dissection probe facilitates passing over lateral branch vessels encountered along the course of the artery being isolated. When the artery and side branches are completely free of connecting tissue, the cannula with endoscope and dissection probe is removed 1515 from the working cavity.

Figure 14:
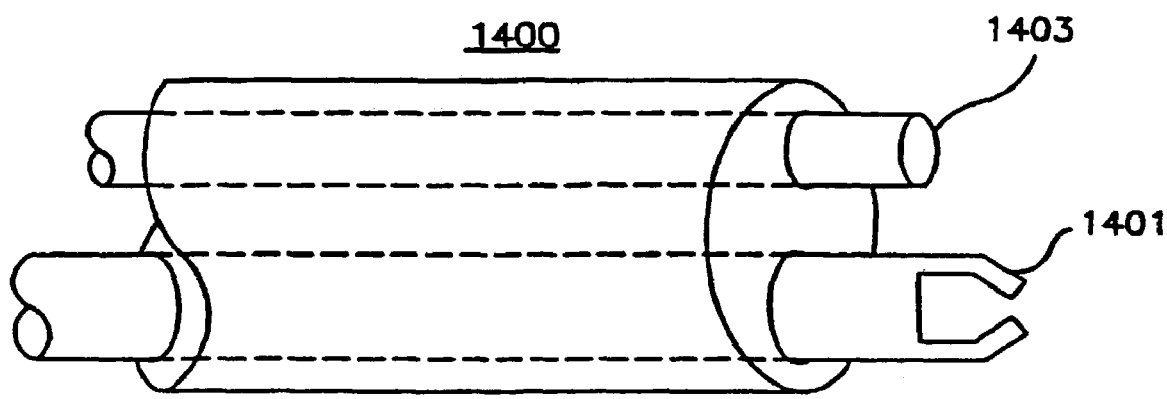
FIG. 14 is a partial pictorial view of a viewing, multiple-clip applier for use in the method of the present invention.

Thereafter, a viewing, multiple-clip applier, as illustrated in FIG. 14, including a clip applier 1401 and an endoscope 1403, and having a circular cross section may be inserted 1517 through the trocar port for placing two surgical clips on each side branch of the isolated artery 1519, spaced sufficiently to divide the branch vessel therebetween. After all side-branch vessels are clipped in this manner, the viewing, multiple-clip applier is completely removed 1521. Alternatively, a two-port, trocar gas seal may be attached to the blunt tip trocar and an endoscope may be inserted through one port with a clip applier or electrocauterizer inserted through the other port for clipping or otherwise occluding the side-branch vessels. The two-port seal for the blunt tip trocar facilitates removal of only the clip applier and replacement thereof by scissor blades that can be manipulated proximally to cut and divide 1523 each of the side branch vessels between the clips that were previously placed or through electrocauterized segment that was prepared while viewing through the endoscope 1403. Thereafter, the scissor blades may be removed, and the internal mammary artery thus isolated may then be used to revascularize diseased coronary arteries 1525, for example, by grafting a transected free end of the isolated internal mammary artery to the left anterior descending coronary artery downstream of a significant stenotic occlusion.

Figure 13A:
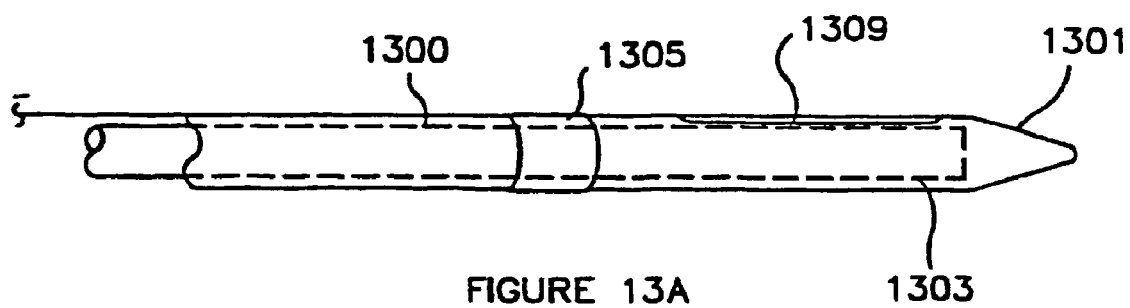
FIGS. 13A and 13B are side views illustrating, respectively, retracted and extended configurations of another embodiment of the tissue separating cannula of the present invention.
Figure 13B:
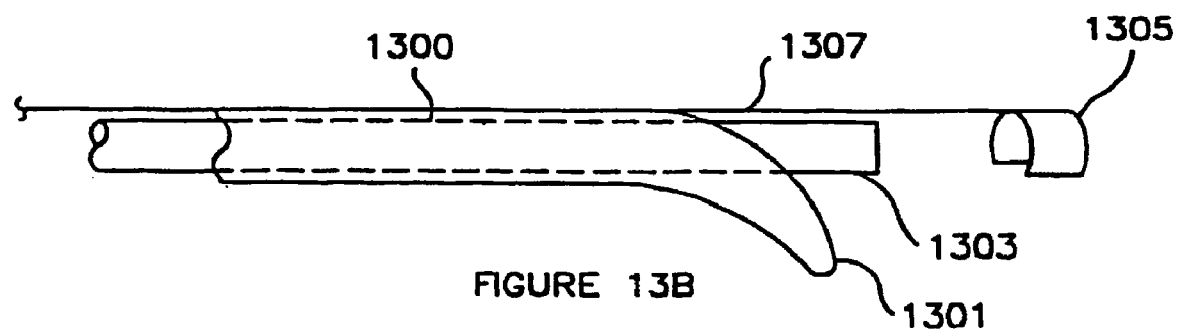

Referring now to FIGS. 13A and 13B, there are shown side views of retracted and extended configurations of another embodiment of the dissection cannula according to the present invention. This embodiment includes a blunt, tapered tip 1301 which deflects to one side of the endoscope 1303 to allow visualization outside of the cannula 1300 during vessel dissection and isolation. The dissection probe 1305 may reside adjacent to the cannula body 1300, proximal to the tapered tip 1301, and extend forward to dissect around the vessel being harvested and its side branches. The dissection probe shaft 1307 may run through a separate lumen in the cannula body 1300. The cannula body 1300 may contain an intrinsic curvature, and contain a port 1309 on the side of the cannula body near the tip, for exit of the endoscope 1303. The cannula body which has a normally curved configuration, straightens out upon introduction of a rigid, straight endoscope 1303. Partial retraction of the endoscope 1303 allows the cannula to curve, and the endoscope is advanced through the side port 1309 in the cannula body 1300 to view outside of the deflected cannula tip 1301.

Figure 17:
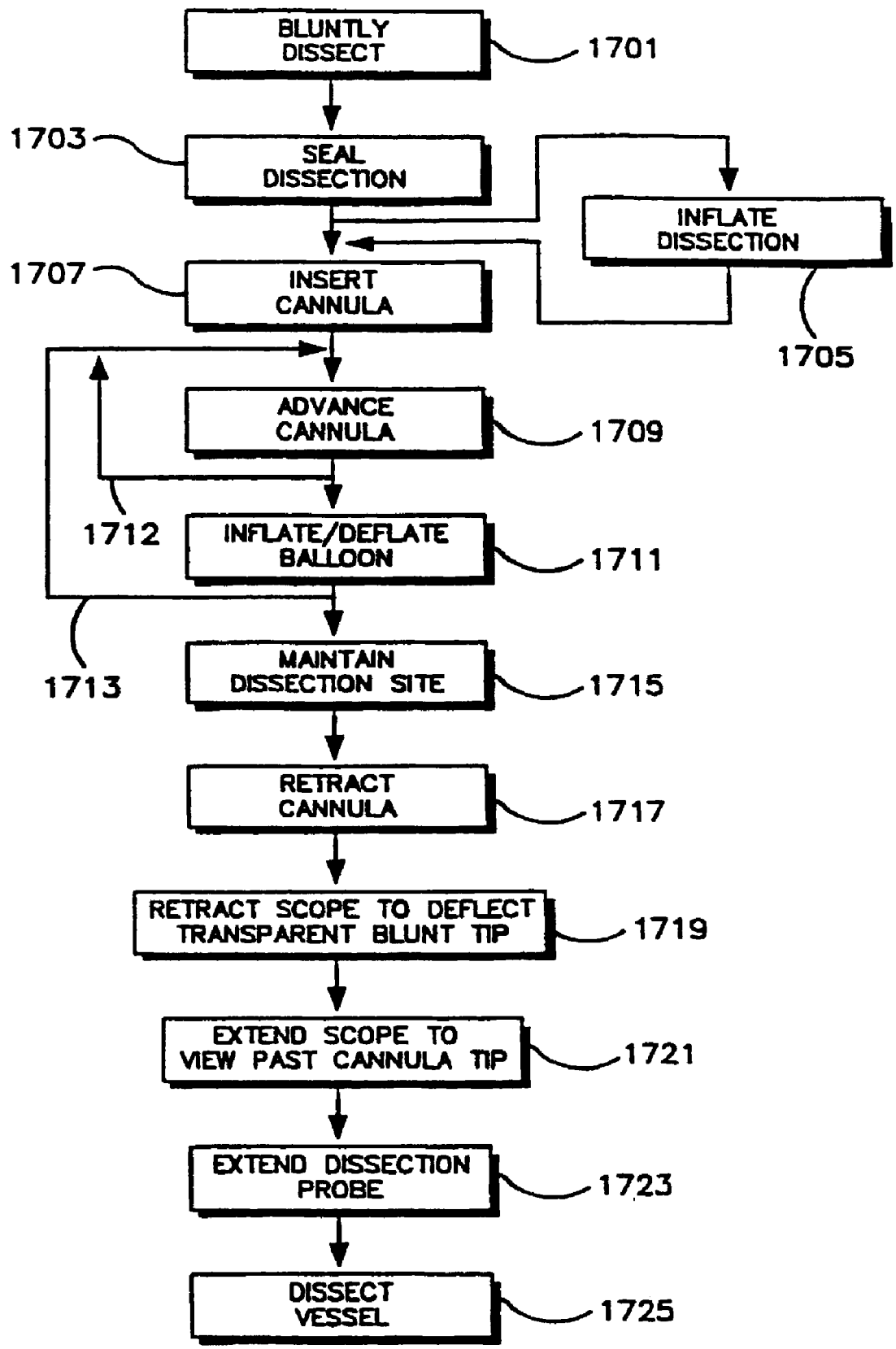
FIG. 17 is a flow chart illustrating the procedures involved with the cannula of FIGS. 13A and 13B.

A surgical procedure involving the cannula 1300 shown in FIG. 13 is illustrated in the flow chart of FIG. 17. Specifically, an initial incision and blunt dissection is performed 1701 to prepare an initial dissected cavity. The cavity may then be sealed 1703 in conventional manner and inflated 1705 to facilitate insertion of the cannula 1300 that is inserted into the cavity 1707 through a conventional gas-tight seal. The cannula is advanced 1709 and a perimeter balloon 128 on the cannula is inflated 1711 to expand the dissected cavity, and is then deflated to facilitate further advancement of the cannula and reinflation of the balloon. This sequence is repeated 1712, 1713 until the dissected cavity of sufficient size or length is formed along the vessel of interest. The dissected cavity is maintained 1715 by insufflation or mechanical traction or otherwise, as previously described, and the cannula may be retracted 1717 to a selected location in the cavity at which the endoscope 1303 may be retracted 1719 relative to the body of the cannula 1300 in order to permit deflection of the blunt tip 1301 away from the tip of the endoscope, as shown in FIG. 13B. Thereafter, the endoscope 1303 may be extended 1721 to view past the blunt tip 1301, and the dissection probe 1305 may also be extended 1723 and manipulated within the dissected cavity to dissect the vessel of interest 1725 from remaining connective tissue.

Figure 16:
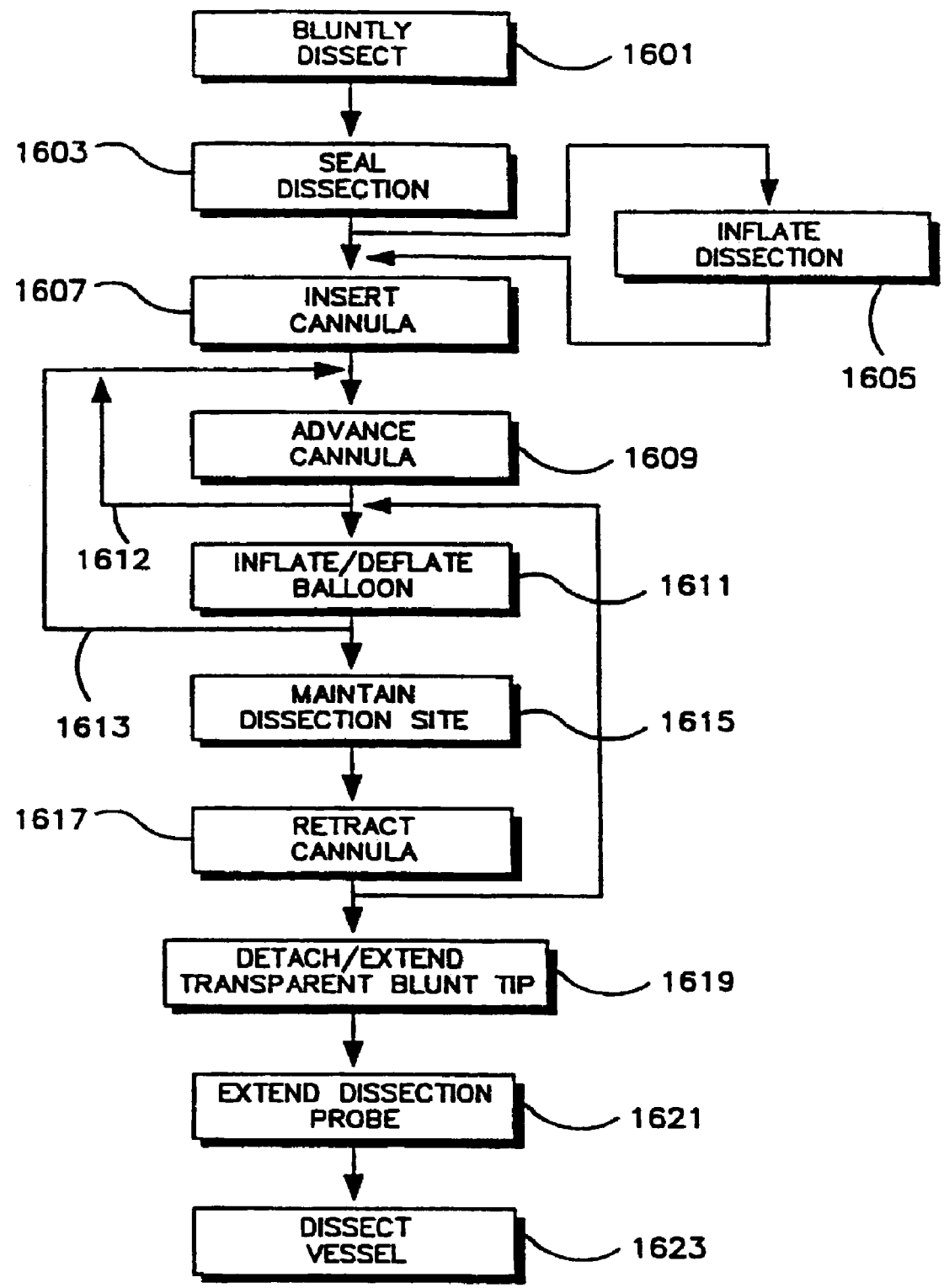
FIG. 16 is a flow chart illustrating the procedures involved with the cannula of FIGS. 9A and 9B.

Referring now to the flow chart of FIG. 16, a surgical procedure involving the cannula 900 shown in FIG. 9A includes making an initial incision and blunt dissection 1601 to form an initial dissected cavity. The cavity may then be sealed 1603 in conventional manner and inflated 1605 to facilitate insertion 1607 of the cannula 900 into the cavity through a conventional gas-tight seal. The cannula 900 is advanced 1609 and a perimeter balloon 901 on the cannula is inflated 1611 to expand the dissected cavity, and is deflated to facilitate further advancement of the cannula, and reinflation of the balloon. This sequence is repeated 1612, 1613 until the dissected cavity of sufficient size or length is formed along the vessel of interest. The dissected cavity is maintained 1615 in a manner as previously described, and the cannula 900 may be retracted 1617 sufficiently within the dissected cavity to facilitate detaching and/or extending 1619 the blunt tip 903 and facilitating extension 1621 of the dissection probe 907. One or more of the steps 1617, 1619, and 1621 may be repeated while dissecting connecting tissue 1623 to harvest the vessel of interest.

Therefore, the cannulas and dissection probes and associated surgical procedures facilitate blunt dissection of a working cavity along a vessel of interest, with visualization of the tissue being dissected through a blunt tip of transparent material and selected optical configuration positioned on the forward end of the cannula. Selective remote deployment and remote manipulation of a dissection probe carried on the cannula facilitates dissection of tissue around the vessel of interest and around side branch vessels along the vessel of interest being harvested from within and along the working cavity of dissected tissue.

What is claimed is:

1. A method for endoscopic harvesting a selected segment of a blood vessel using an elongated cannula having a rigid tip on a distal end for bluntly dissecting tissue, the method comprising:
   forming an incision in skin overlying the vessel to expose the vessel;
   inserting the rigid tip of the cannula in the incision adjacent the exposed vessel;
   advancing the rigid tip of the cannula through tissue along the course of the vessel to bluntly dissect tissue in response to contact with the rigid tip and to separate the vessel from surrounding tissue to form a cavity adjacent the vessel along the selected segment thereof, wherein the rigid tip is advanced from a proximal end of the segment being harvested to a distal end of the segment being harvested;
   sealing the incision and insufflating with fluid under pressure the cavity formed by advancing the rigid tip through tissues;
   occluding and cutting side branches from the vessel along the selected segment thereof; and
   sealing and cutting the vessel at the proximal and distal ends of the selected segment within the cavity for removal through the incision.

2. The method according to claim 1 performed with a cannula having a rigid transparent tip on the distal end and having an endoscope disposed within the cannula for visualization from within and through the rigid transparent tip, wherein:
   advancing of the rigid tip of the cannula along the course of the vessel includes visualizing from within and through the rigid tip the tissue in direct contact therewith during the dissection by the rigid tip that separates the vessel from surrounding tissue.

3. A method for endoscopic harvesting of a selected segment of a blood vessel using an elongated cannula having a rigid tip on a distal end thereof for bluntly dissecting tissue, the method comprising:
   forming an incision in skin overlying the vessel to expose the vessel;
   sealing the incision and insufflating a perivascular region adjacent the vessel near the incision with fluid under pressure;
   advancing the rigid tip of the cannula along the segment of the vessel to dissect tissue under insufflation in response to contact with the rigid tip and to separate the vessel from surrounding tissue to form a cavity of selected dimensions adjacent the vessel along the selected segment thereof, wherein the rigid tip is advanced from a proximal end of the segment being harvested to a distal end of the segment being harvested;
   selectively expanding the dimensions of the cavity adjacent the vessel along the selected segment thereof;
   occluding and cutting side branches from the vessel along the selected segment thereof; and sealing and cutting the vessel at the proximal and distal ends of the selected segment thereof for removal from the cavity through the incision.

4. The method according to claim 3 including:
installing a trocar to seal the incision; and
insufflating of the perivascular region is through the trocar to increase the dimensions of the cavity.

5. A method for dissecting tissue from a segment of a vessel in the body of a patient using an elongated element having a rigid dissecting tip at a distal end thereof, the method comprising the steps of:
dissecting by the rigid tip tissue adjacent the segment of the vessel to form a cavity in tissue adjacent the vessel using the elongated element with the rigid tip in contact with the vessel along the course of the segment of the vessel from a proximal end of the segment of the vessel to a distal end of the segment of the vessel; and
visualizing from within the cavity the dissection of tissue by the rigid tip from the segment of the vessel to release the segment of vessel from connective tissue.

6. The method of claim 5 in which an endoscope is disposed to visualize from within and through the rigid tip, the tissue being dissected by the rigid tip, and includes a rigid dissection probe manipulatable within the visualization of the endoscope, wherein the step of visualizing includes manipulating the dissection probe ahead of the endoscope along the course of the segment of the vessel from within the cavity to dissect connective tissue along the vessel and around side branches thereof that are visualized from within and along the cavity adjacent the course of the segment of vessel.

7. The method of claim 5, wherein the vessel comprises an artery.

8. The method of claim 5, wherein the vessel comprises a vein.

9. A method for endoscopic harvesting of a segment of a blood vessel using a rigid elongated cannula having a distal end and a rigid element disposed thereat for bluntly dissecting tissue, the method comprising:
forming an incision in skin overlying the vessel to expose the vessel;
inserting the distal end of the cannula in the incision adjacent the exposed vessel;
advancing the distal end of the rigid elongated cannula to position the rigid element near the vessel along the course thereof for bluntly dissecting tissue away from the segment of the vessel by the rigid element to separate the vessel from surrounding tissue to form a cavity adjacent the segment of the vessel, wherein the distal end of the rigid elongated cannula is advanced from a proximal end of the segment being harvested to a distal end of the segment being harvested;
insufflating the cavity with fluid under pressure;
occluding and cutting side branches from the segment of the vessel; and
cutting the vessel at the proximal and distal ends of the segment of the vessel for removal thereof from within the cavity.

10. A method for endoscopic harvesting of a segment of a blood vessel using a rigid elongated cannula having a distal end and a rigid element disposed thereat for bluntly dissecting tissue, the method comprising:
forming an incision in skin overlying the vessel to expose the vessel;
inserting the distal end of the cannula in the incision adjacent the exposed vessel;
advancing the distal end of the rigid elongated cannula to position the rigid element near the vessel along the course thereof for bluntly dissecting tissue away from the segment of the vessel by the rigid element to separate the vessel from surrounding tissue to form a cavity adjacent the segment of the vessel, wherein the distal end of the rigid elongated cannula is advanced from a proximal end of the segment being harvested to a distal end of the segment being harvested;
insufflating the cavity with fluid under pressure;
occluding and cutting side branches from the segment of the vessel; and
cutting the vessel at the proximal and distal ends of the segment of the vessel for removal thereof from within the cavity;
wherein the rigid elongated cannula includes the rigid element disposed near the distal end of the cannula for selective movement relative thereto in response to manipulation of linkage coupled to the rigid element from a proximal end of the rigid elongated cannula, and the method includes the additional steps of:
extending the rigid element relative to the distal end of the cannula; and
selectively dissecting tissue with the rigid element forward of the distal end of the cannula under visualization from near the distal end of the cannula in response to manual manipulation of the linkage to the rigid element from near the proximal end of the cannula.

11. The method according to claim 9 in which: the rigid element advanced with the distal end of the elongated cannula bluntly dissects tissue along the course of the vessel over substantially the length of the cannula for separating tissue from the vessel to form the cavity therealong; and comprising:
selectively expanding dimensions of the cavity adjacent the segment of the vessel from dimensions of the cavity formed by the rigid element advancing with the distal end of cannula along the segment of the vessel; and
occluding and cutting side branches from the segment of the vessel, and cutting the proximal and distal ends of the segment of vessel within the expanded cavity for removal of the segment of vessel from the cavity.

12. A method for harvesting of a segment of a blood vessel using a rigid elongated cannula having a distal end and a rigid element disposed thereat for bluntly dissecting tissue, the method comprising:
forming an incision in skin overlying the vessel to expose the vessel;
insufflating a perivascular region adjacent the vessel near the incision with fluid under pressure;
advancing the distal end of the rigid elongated cannula to position the rigid element near the vessel along the course thereof for dissecting tissue away from the segment of the vessel by the rigid element to separate the segment of the vessel from surrounding tissue to form a cavity adjacent the segment of the vessel, wherein the distal end of the rigid elongated cannula is advanced from a proximal end of the segment being harvested to a distal end of the segment being harvested;
selectively expanding the dimensions of the cavity adjacent the segment of the vessel;
occluding and cutting side branches from the segment of the vessel; and
cutting the vessel at the proximal and distal ends of the segment of the vessel for removal from within the cavity.

13. The method according to claim 12 in which the rigid element includes an attached blunt dissection tip that is advanced through tissue near the vessel for dissecting tissue away from the segment of the vessel along the course thereof to form an elongated cavity adjacent the vessel.

14. The method according to claim 13 in which the blunt dissection tip for advancing through tissue is configured for substantially atraumatic blunt dissection of tissue and includes a shape selected from the group consisting of conical, spherical, straight tapered, and curved tapered.

15. A method for harvesting a segment of a vessel in the body of a patient using a cannula having a tissue-dissecting rigid tip at the distal end thereof and having a balloon attached to an exterior wall of the cannula at least near a distal end thereof and including an endoscope disposed within the cannula for visualizing tissue in proximity of the tissue-dissecting rigid tip, the method comprising the steps of:
  forming an initial incision and bluntly dissecting an initial cavity at a location in the body of a patient near the vessel;
  inserting the tissue-dissecting rigid tip at the distal end of the cannula into the incision and advancing the rigid tip on the distal end of the cannula for separating the tissue in contact with the tissue-dissecting rigid tip along the segment of the vessel as visualized through the endoscope, wherein the rigid tip is advanced from a proximal end of the segment being harvested to a distal end of the segment being harvested;
  selectively inflating the balloon to expand the cavity formed in tissue by the tissue-dissecting rigid tip along the segment of the vessel;
  selectively deflating the balloon within the expanded cavity to facilitate advancing the cannula and tissue-dissecting rigid tip within the expanded cavity formed in tissue by the rigid tip along the segment of the vessel; and
  selectively manipulating connecting tissue along the segment of the vessel as visualized through the endoscope to isolate the segment of the vessel for harvest from within the cavity in the body.

16. The method according to claim 15 in which the step of manipulating includes dissecting tissue within the expanded cavity along the vessel and around side vessels that laterally extend therefrom to dissect connecting tissue and isolate the segment of vessel within the expanded cavity.

17. A method for harvesting a selected segment of a blood vessel using an elongated cannula having a blunt distal end, the method comprising:
  advancing the blunt distal end from a proximal portion of the segment to a distal portion of the segment;
  activating the blunt distal end of the cannula through tissue along the course of the selected segment of the blood vessel to be harvested to bluntly dissect tissue in response to contact with the blunt distal end and to separate the vessel from surrounding tissue to form an elongated cavity adjacent the vessel along the selected segment thereof;
  endoscopically visualizing through the distal end within the cavity the dissection of tissue by the blunt tip from the selected segment of the blood vessel;
  removing the cannula from the elongated cavity; and then
  severing at least one end of the selected segment of the blood vessel and using the blood vessel as a bypass graft.

18. The method of claim 17, further comprising:
  selectively expanding the dimensions of the elongated cavity adjacent the vessel along the selected segment thereof.

19. The method of claim 18, in which the step of selectively expanding comprises inflating a balloon mounted on the cannula.

20. The method of claim 17, further comprising:
  forming an incision in skin overlying the blood vessel;
  sealing the incision and insufflating the elongated cavity with fluid under pressure; and
  inserting an instrument through the sealed incision to sever and close off side branches from the blood vessel.

21. The method of claim 17, further comprising:
  after removing the cannula, severing both ends of the selected segment of the blood vessel and removing the selected segment from within the cavity.

22. A method for harvesting a selected segment of a blood vessel using an elongated cannula having a closed, blunt distal end, the method comprising:
  displacing the blunt distal end of the cannula to a first location along the selected segment of the blood vessel to bluntly dissect tissue and separate the vessel from surrounding tissue and form a cavity;
  expanding an inflatable member mounted near the distal end of the cannula to expand the dimensions of the cavity at the first location;
  displacing the distal end of the cannula to a second location along the selected segment of the blood vessel to bluntly dissect tissue and separate the vessel from surrounding tissue and increase the length of the cavity, wherein the second location is at a distal portion of the selected segment being harvested; and
  expanding the inflatable member to expand the dimensions of the cavity at the second location.

23. The method of claim 22, further comprising:
  endoscopically visualizing through the distal end within the cavity the dissection of tissue by the blunt distal end of the cannula and the inflatable member.

24. The method of claim 23, wherein the step of endoscopically visualizing comprises:
  viewing the progression of the blunt distal end of the cannula through an imaging device positioned within the cannula to provide visual imaging through the blunt distal end.

25. The method of claim 22, further including:
  forming an incision in skin overlying the blood vessel;
  dissecting through subcutaneous tissue to expose the blood vessel and create a cavity adjacent the blood vessel;
  sealing the incision with a port disposed to form a sliding seal with the cannula; and
  insufflating the cavity with fluid under pressure.

26. The method of claim 25, further comprising:
  slidably passing the cannula through the port to form a sliding seal therebetween; and
  insufflating of the cavity with fluid under pressure supplied through the port.

27. A method of harvesting a selected segment of a blood vessel using an elongated cannula having a blunt distal end, the method comprising:
  forming an incision in the skin overlying the blood vessel;
  dissecting through subcutaneous tissue to expose the blood vessel and form a cavity thereabout;
  forming a gas tight seal in the incision;
  infusing gas through the gas tight seal to expand the cavity formed around the blood vessel; and
  inserting the elongated cannula through the gas tight seal and advancing the blunt distal end through the tissue surrounding the blood vessel for dissecting tissue to form the cavity along the blood vessel, wherein the blunt distal end is advanced from a proximal end of the segment being harvested to a distal end of the segment being harvested.

28. The method of claim 27, in which forming the gas tight seal in the incision comprises inserting into the incision a blunt tip trocar configured to form a gas tight seal in the incision and an inner sliding gas tight seal around the elongated cannula sliding therethrough.

* * * * *